(12) United States Patent
Miyazaki et al.

(10) Patent No.: US 12,428,390 B2
(45) Date of Patent: Sep. 30, 2025

(54) CHROMENE COMPOUND AND PHOTOCHROMIC OPTICAL ARTICLE

(71) Applicant: TOKUYAMA CORPORATION, Shunan (JP)

(72) Inventors: Masayuki Miyazaki, Shunan (JP); Junji Takenaka, Shunan (JP); Junji Momoda, Shunan (JP)

(73) Assignee: TOKUYAMA CORPORATION, Yamaguchi (JP)

( * ) Notice: Subject to any disclaimer, the term of this patent is extended or adjusted under 35 U.S.C. 154(b) by 934 days.

(21) Appl. No.: 17/613,129

(22) PCT Filed: Jun. 8, 2020

(86) PCT No.: PCT/JP2020/022524
§ 371 (c)(1),
(2) Date: Nov. 22, 2021

(87) PCT Pub. No.: WO2020/261961
PCT Pub. Date: Dec. 30, 2020

(65) Prior Publication Data
US 2022/0213050 A1 Jul. 7, 2022

(30) Foreign Application Priority Data
Jun. 27, 2019 (JP) .................................. 2019-120178

(51) Int. Cl.
*C07D 311/94* (2006.01)
*C09K 9/02* (2006.01)
*G02C 7/04* (2006.01)
*G02C 7/10* (2006.01)

(52) U.S. Cl.
CPC .............. *C07D 311/94* (2013.01); *C09K 9/02* (2013.01); *G02C 7/102* (2013.01); *C09K 2211/1018* (2013.01)

(58) Field of Classification Search
CPC .................... C07D 311/94; C09K 9/02; C09K 2211/1018; G02C 7/04; G02C 7/102
See application file for complete search history.

(56) References Cited

U.S. PATENT DOCUMENTS

| | | | |
|---|---|---|---|
| 6,113,814 A * | 9/2000 | Gemert ..................... | C09K 9/02 546/281.1 |
| 6,555,028 B2 | 4/2003 | Walters et al. | |
| 6,723,859 B2 | 4/2004 | Kawabata et al. | |
| 7,521,004 B2 | 4/2009 | Momoda et al. | |
| 7,556,750 B2 | 7/2009 | Xiao et al. | |
| 8,147,725 B2 | 4/2012 | Chopra et al. | |
| 8,388,872 B2 | 3/2013 | Chopra et al. | |
| 8,647,538 B2 | 2/2014 | Lu et al. | |
| 9,028,728 B2 | 5/2015 | Bancroft et al. | |
| 9,139,552 B2 | 9/2015 | Xiao et al. | |

(Continued)

FOREIGN PATENT DOCUMENTS

| | | |
|---|---|---|
| CN | 101503484 A | 8/2009 |
| CN | 103172878 A | 6/2013 |
| JP | 2002-524558 A | 8/2002 |
| JP | 2005-514643 A | 5/2005 |
| JP | 2008-535971 A | 9/2008 |

(Continued)

OTHER PUBLICATIONS

Sep. 1, 2020 International Search Report issued in International Patent Application No. PCT/JP2020/022524.
Dec. 28, 2021 International Preliminary Report on Patentability issued in International Patent Application No. PCT/JP2020/022524.
May 25, 2023 Office Action issued in Chinese Patent Application No. 202080047000.0.

*Primary Examiner* — Bijan Ahvazi
(74) *Attorney, Agent, or Firm* — Oliff PLC

(57) ABSTRACT

A chromene compound which can exhibit excellent photochromic properties. The chromene compound is represented by the following formula (1). In the formula, at least one of $R^1$ or $R^2$ represents the group having the radical-polymerizable group, wherein the group having a radical-polymerizable group is represented by the following formula (2) (wherein $R^{10}$ represents a linear or branched alkylene group having 1 to 10 carbon atoms and l represents an integer of from 0 to 50); and the ring Z that is represented by the following formula (Z) and is spiro-bonded to a carbon atom located at position-13 in the formula (1) is preferably an aliphatic cyclic group that may have a substituent, the group having 3 to 20 carbon atoms for forming the ring together with the carbon atom at the 13-position, or the like.

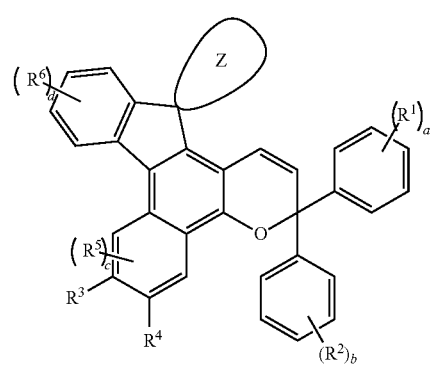

(1)

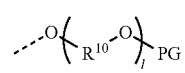

(2)

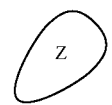

(Z)

9 Claims, No Drawings

(56) References Cited

U.S. PATENT DOCUMENTS

| | | |
|---|---|---|
| 11,401,276 B2 | 8/2022 | Miyazaki et al. |
| 2001/0025948 A1 | 10/2001 | Walters et al. |
| 2002/0133889 A1 | 9/2002 | Molock et al. |
| 2003/0000028 A1 | 1/2003 | Molock et al. |
| 2003/0096117 A1* | 5/2003 | Kawabata .............. G03C 1/685 428/411.1 |
| 2003/0141490 A1 | 7/2003 | Walters et al. |
| 2004/0014995 A1 | 1/2004 | Kawabata et al. |
| 2005/0258408 A1 | 11/2005 | Molock et al. |
| 2006/0226400 A1* | 10/2006 | Xiao .................... C07D 311/78 252/582 |
| 2006/0228557 A1 | 10/2006 | Kim et al. |
| 2007/0001155 A1 | 1/2007 | Walters et al. |
| 2007/0215844 A1* | 9/2007 | Momoda .............. C07D 311/96 252/582 |
| 2009/0032782 A1 | 2/2009 | Kim et al. |
| 2011/0042629 A1 | 2/2011 | Chopra et al. |
| 2012/0132870 A1 | 5/2012 | Xiao et al. |
| 2012/0136148 A1 | 5/2012 | Lu et al. |
| 2012/0145973 A1 | 6/2012 | Bancroft et al. |
| 2012/0145975 A1 | 6/2012 | Chopra et al. |
| 2020/0190106 A1* | 6/2020 | Miyazaki ............... C08K 5/357 |
| 2022/0244428 A1* | 8/2022 | Tomida .................... A61F 2/16 |

FOREIGN PATENT DOCUMENTS

| | | | |
|---|---|---|---|
| JP | 2008-536179 A | | 9/2008 |
| JP | 2008-537746 A | | 9/2008 |
| JP | 2018062496 A | * | 4/2018 ........... C07D 311/96 |
| WO | 00/15629 A1 | | 3/2000 |
| WO | 01/60811 A1 | | 8/2001 |
| WO | 03/056390 A2 | | 7/2003 |
| WO | 2005/028465 A1 | | 3/2005 |
| WO | 2006/110219 A1 | | 10/2006 |
| WO | 2019/013249 A1 | | 1/2019 |

\* cited by examiner

CHROMENE COMPOUND AND PHOTOCHROMIC OPTICAL ARTICLE

TECHNICAL FIELD

The present invention relates to a novel chromene compound having a polymerizable group, and a novel photochromic optical article obtained by polymerizing the chromene compound.

BACKGROUND ART

Photochromism refers to a reversible reaction in which when a certain compound is irradiated with light containing UV light, such as sunlight or light from a mercury lamp, its color immediately changes, and when the light irradiation is stopped and the compound is placed in a dark place, the color is returned to the original color by heat. A photochromic compound having the property has been used in an application where reversible discoloration or darkening induced by daylight is desired, for example, as a material for a photochromic glass lens or a photochromic contact lens.

A photochromic compound to be used in a plastic glass lens has been generally required to have the following characteristics:

(1) the coloring degree of the compound in a visible light region before UV irradiation (hereinafter referred to as "initial coloring") is small;
(2) the rate at which the color development density thereof becomes saturated after the start of the UV irradiation is fast (hereinafter, such characteristic may be expressed by the phrase "color development sensitivity is high");
(3) the rate at which the compound returns to its original state after the stop of the UV irradiation (hereinafter referred to as "color fading rate") is fast;
(4) the repetition durability of the reversible action is satisfactory; and
(5) in order that the dispersibility of the compound in a host material to be used may be high, the compound is dissolved at a high concentration in a monomer composition that becomes the host material after its curing.

In addition, when a photochromic characteristic is imparted to a contact lens, a photochromic compound to be used in the contact lens has been required to have performance higher than that of the photochromic compound to be used in a glass lens in addition to the characteristics because the contact lens is brought into direct contact with an eye. An example of the required performance is (6) such a characteristic that the photochromic compound is not eluted when turned into the contact lens. In particular, with regard to the elution of the photochromic compound at the time of the formation of the contact lens, adverse effects on an eye due to the elution and diffusion thereof into the eye become problems.

A photochromic compound having a monomer structure (polymerizable group) copolymerizable with a contact lens material monomer has been developed as a method of solving such problems. Specifically, there are disclosures of chromene compounds represented by the following formulae (X), (Y), and (Z), the compounds each having a polymerizable group (see Patent Literatures 1, 2, and 3). Each of those chromene compounds has a polymerizable group, and hence copolymerizes with any other monomer to be captured in a polymer chain. Accordingly, when each of the compounds is turned into a contact lens, its elution can be reduced.

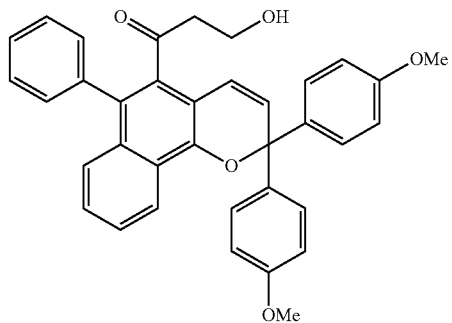
(X)

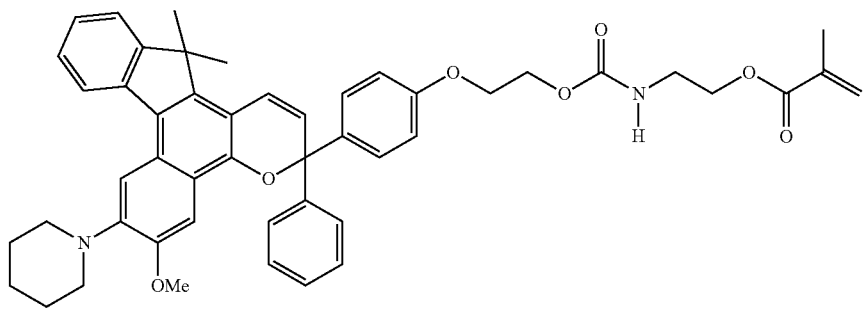
(Y)

-continued

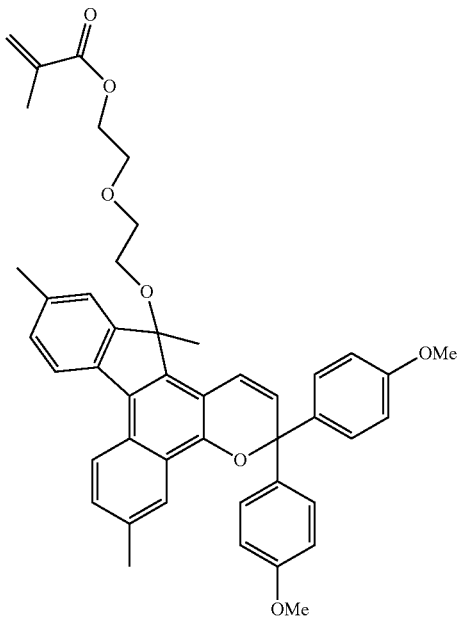

(Z)

CITATION LIST

Patent Literature

[PTL 1] WO 2000/015629 A1
[PTL 2] WO 2006/110219 A1
[PTL 3] WO 2003/056390 A2

SUMMARY OF INVENTION

Technical Problem

However, the related-art method has been susceptible to improvement in terms of the following. For example, the chromene compound represented by the formula (X) has been susceptible to improvement because the polymerizable group of the chromene compound represented by the formula (X) is a hydroxy group, and hence other monomers to be copolymerized therewith are limited and the elution thereof cannot be sufficiently suppressed.

In addition, a compound substituted with a polymerizable group at its 13-position like the chromene compound represented by the formula (Z) has been susceptible to improvement because the repetition durability of the compound is low, though the elution thereof can be suppressed.

Further, an investigation by the inventors of the present invention has found that the chromene compounds represented by the formulae (Y) and (Z) cannot exhibit sufficient characteristics when used in contact lens applications. That is, the investigation has found that when a chromene compound is used in the contact lens applications, the following effects are additionally required. Specifically, the following characteristics are required:

(7) the compound needs to have a high color development density at around the surface temperature (from 33° C. to 38° C.) of an eye; and (8) when a person wearing a contact lens moves to a dark place, such as the inside of a tunnel, the compound needs to have such high-speed responsiveness that its color fading is completed within from several seconds to several tens of seconds.

However, applications where the above-mentioned effects (6), (7), and (8) are useful are not limited to the contact lens applications. That is, when an effect, such as the effect (6), is exhibited, no elution of a photochromic compound occurs even in a glass lens, and hence adverse effects on eyes can be further suppressed. In addition, when the compound exhibits the effect (7) or (8), the lens can be used as a photochromic glass lens having performance higher than ever before in a hot and shiny area, such as a summer resort. In addition, when the compound is capable of high-speed response, its value as a photochromic glass lens is improved, and moreover, the possibility that the compound is used in various applications becomes higher.

Accordingly, an object of the present invention is to provide a chromene compound, which is copolymerizable with any other monomer, can suppress the elution of the photochromic compound (chromene compound) itself from the resultant polymer (photochromic optical article), and has a desired photochromic property.

Solution to Problem

The inventors of the present invention have made extensive investigations for solving the problems. In addition, the inventors have investigated various substituents and the bonding positions of the substituents through use of the fact that the bonding of the various substituents to the indenonaphthopyran skeleton of a chromene compound enables the compound to exhibit photochromic characteristics in accordance with respective applications. As a result, the inventors have found that the problems can be solved by using the following groups out of numberless combinations of the kinds and substitution positions of the substituents: a specific cyclic group is used as a group bonded to a carbon atom at the 13-position of the indenonaphthopyran skeleton (formally an "indeno(2,1-f)naphtho(1,2-b)pyran structure");

and a group having a radical-polymerizable group is bonded to the 3-position thereof. Thus, the inventors have completed the present invention.

That is, according to a first embodiment of the present invention, there is provided a chromene compound represented by the following formula (1):

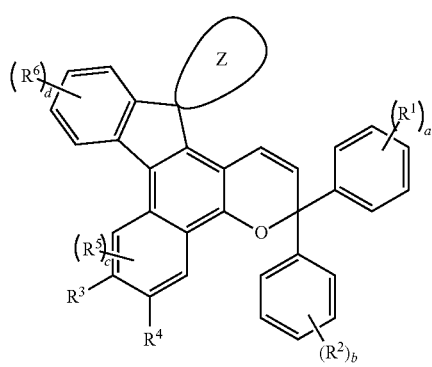

where $R^1$ and $R^2$ each independently represent a group having a radical-polymerizable group, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a heterocyclic group, a cyano group, a halogen atom, an alkylthio group having 1 to 6 carbon atoms, or an arylthio group having 6 to 10 carbon atoms that may have a substituent, "a" represents an integer of from 0 to 5, and "b" represents an integer of from 0 to 5, provided that a+b=1 to 10, at least one of $R^1$ or $R^2$ represents the group having the radical-polymerizable group, the group having the radical-polymerizable group is a group represented by the following formula (2):

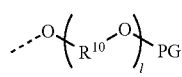

(where $R^{10}$ represents a linear or branched alkylene group having 1 to 10 carbon atoms, "l" represents an integer of from 0 to 50, and when "l" represents 2 or more, unit groups in "l" pairs of parentheses may be groups identical to or different from each other, and PG represents the radical-polymerizable group), a ring Z represented by the following formula (Z), the ring being spiro-bonded to a carbon atom at a 13-position of the formula (1)

is an aliphatic cyclic group that may have a substituent, the group having 3 to 20 carbon atoms for forming the ring together with the carbon atom at the 13-position, a condensed polycyclic group obtained by condensing the aliphatic cyclic group with an aromatic ring or an aromatic heterocycle that may have a substituent, a heterocyclic group that may have a substituent, the group having 3 to 20 atoms for forming the ring together with the carbon atom at the 13-position, or a condensed polycyclic group obtained by condensing the heterocyclic group with an aromatic ring or an aromatic heterocycle that may have a substituent, $R^3$ represents a hydrogen atom, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, a cyano group, a halogen atom, an alkylthio group having 1 to 6 carbon atoms, an arylthio group having 6 to 10 carbon atoms that may have a substituent, a nitro group, a formyl group, a hydroxycarbonyl group, an alkylcarbonyl group having 2 to 7 carbon atoms, an alkoxycarbonyl group having 2 to 7 carbon atoms, an aralkyl group having 7 to 11 carbon atoms that may have a substituent, an aralkoxy group having 7 to 11 carbon atoms that may have a substituent, an aryloxy group having 6 to 12 carbon atoms that may have a substituent, an aryl group having 6 to 12 carbon atoms that may have a substituent, a heteroaryl group having 3 to 12 carbon atoms that may have a substituent, a thiol group, an alkoxyalkylthio group having 2 to 9 carbon atoms, a haloalkylthio group having 1 to 6 carbon atoms, or a cycloalkylthio group having 3 to 8 carbon atoms, $R^4$ represents a hydrogen atom, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a heterocyclic group, a cyano group, a halogen atom, an alkylthio group having 1 to 6 carbon atoms, an arylthio group having 6 to 10 carbon atoms that may have a substituent, a nitro group, a formyl group, a hydroxycarbonyl group, an alkylcarbonyl group having 2 to 7 carbon atoms, an alkoxycarbonyl group having 2 to 7 carbon atoms, an aralkyl group having 7 to 11 carbon atoms that may have a substituent, an aralkoxy group having 7 to 11 carbon atoms that may have a substituent, an aryloxy group having 6 to 12 carbon atoms that may have a substituent, an aryl group having 6 to 12 carbon atoms that may have a substituent, a heteroaryl group having 3 to 12 carbon atoms that may have a substituent, a thiol group, an alkoxyalkylthio group having 2 to 9 carbon atoms, a haloalkylthio group having 1 to 6 carbon atoms, or a cycloalkylthio group having 3 to 8 carbon atoms, and $R^3$ and $R^4$ may form a ring represented by the following formula (3) together:

[where * represents a carbon atom at a 6-position or a 7-position thereof, one, or each of both, of X and Y represents a sulfur atom, a methylene group, an oxygen atom, or a group represented by the following formula:

(where R⁹ represents a hydrogen atom, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an aryl group having 6 to 12 carbon atoms that may have a substituent, or a heteroaryl group having 3 to 12 carbon atoms that may have a substituent), R⁷ and R⁸ each independently represent a hydroxy group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group, a cyano group, a nitro group, a formyl group, a hydroxycarbonyl group, an alkylcarbonyl group having 2 to 7 carbon atoms, an alkoxycarbonyl group having 2 to 7 carbon atoms, a halogen atom, an aralkyl group having 7 to 11 carbon atoms that may have a substituent, an aralkoxy group having 7 to 11 carbon atoms that may have a substituent, an aryl group having 6 to 12 carbon atoms that may have a substituent, a thiol group, an alkylthio group having 1 to 6 carbon atoms, an alkoxyalkylthio group having 2 to 9 carbon atoms, a haloalkylthio group having 1 to 6 carbon atoms, a cycloalkylthio group having 3 to 8 carbon atoms, or an arylthio group having 6 to 10 carbon atoms that may have a substituent, and R⁷ and R⁸ may form an aliphatic ring together with a carbon atom to which R⁷ and R⁸ are bonded, and "e" represents an integer of from 1 to 3], R⁵ represents a hydroxy group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group, a cyano group, a nitro group, a formyl group, a hydroxycarbonyl group, an alkylcarbonyl group having 2 to 7 carbon atoms, an alkoxycarbonyl group having 2 to 7 carbon atoms, a halogen atom, an aralkyl group having 7 to 11 carbon atoms that may have a substituent, an aralkoxy group having 7 to 11 carbon atoms that may have a substituent, an aryl group having 6 to 12 carbon atoms that may have a substituent, a thiol group, an alkylthio group having 1 to 6 carbon atoms, an alkoxyalkylthio group having 2 to 9 carbon atoms, a haloalkylthio group having 1 to 6 carbon atoms, a cycloalkylthio group having 3 to 8 carbon atoms, or an arylthio group having 6 to 10 carbon atoms that may have a substituent, "c" represents an integer of from 0 to 2, and when "c" represents 2, R⁵s may represent groups identical to or different from each other, R⁶ represents a hydroxy group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group, a halogen atom, an aralkyl group having 7 to 11 carbon atoms that may have a substituent, an aralkoxy group having 7 to 11 carbon atoms that may have a substituent, a thiol group, an alkylthio group having 1 to 6 carbon atoms, an alkoxyalkylthio group having 2 to 9 carbon atoms, a haloalkylthio group having 1 to 6 carbon atoms, a cycloalkylthio group having 3 to 8 carbon atoms, or an arylthio group having 6 to 10 carbon atoms that may have a substituent, and "d" represents an integer of from 0 to 4, and when "d" represents 2 or more, R⁶s may represent groups identical to or different from each other.

According to a second embodiment of the present invention, there is provided a photochromic curable composition, including: the chromene compound according to the first embodiment of the present invention; and a polymerizable monomer except the chromene compound.

According to a third embodiment of the present invention, there is provided a photochromic optical article, including a polymer of the chromene compound according to the first embodiment of the present invention.

According to a fourth embodiment of the present invention, there is provided a photochromic optical article, including a polymer of the photochromic curable composition according to the second embodiment of the present invention.

In the fourth embodiment of the present invention, it is preferred that the photochromic optical article include, as at least part of constituent members, a polymer molded body obtained by polymerizing the photochromic curable composition. In addition, it is preferred that the photochromic optical article include: an optical substrate; and a polymer film obtained by polymerizing the photochromic curable composition, the polymer film serving as a coating layer configured to coat at least part of the optical substrate.

Advantageous Effects of Invention

The chromene compound of the present invention has the specific ring Z (cyclic group containing the carbon atom at its 13-position) and has at least one radical-polymerizable group in the phenyl groups substituting its 3-position, and hence exhibits an excellent effect. In particular, when the structure is adopted, a high polymerization degree is obtained at the time of the copolymerization of the chromene compound with any other monomer, and the elution of the chromene compound itself can be suppressed in the resultant polymer. In addition, the resultant polymer becomes a photochromic optical article having a high color development density and a fast color fading rate in a specific temperature range (e.g., from 33° C. or more to 38° C. or less, the temperatures being higher than room temperature).

The chromene compound of the present invention has the specific ring Z and has the radical-polymerizable group at a specific position, and cannot exhibit an excellent characteristic when one of the groups does not satisfy the requirement of the present invention. None of the related-art compounds has simultaneously satisfied requirements concerning those two substituents.

Accordingly, for example, when the chromene compound of the present invention is used in a photochromic contact lens, there can be produced a photochromic contact lens, which can suppress the elution of the photochromic compound (chromene compound), and has a high color development density and a fast color fading rate even at a temperature around the surface temperature of an eye.

In addition, when the compound is used in a photochromic glass lens, the lens can be used in a high-temperature area and can correspond to high-speed response, and hence has a high added value.

DESCRIPTION OF EMBODIMENTS

A chromene compound of the present invention has a 3,3-diphenylindenonaphthopyran structure represented by the following formula (1) as a basic skeleton (hereinafter sometimes simply referred to as "indenonaphthopyran skeleton").

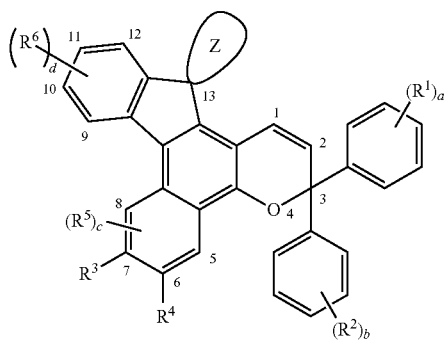

In general, a chromene compound having an indenonaphthopyran structure is known to show an excellent photochromic characteristic. Specific substituents are hereinafter described in due order.

<$R^1$ and $R^2$>

Both of $R^1$ and $R^2$ represent substituents substituting phenyl groups bonded to a carbon atom at the 3-position of the indenonaphthopyran skeleton.

$R^1$ and $R^2$ each independently represent a group having a radical-polymerizable group, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a heterocyclic group, a cyano group, a halogen atom, an alkylthio group having 1 to 6 carbon atoms, or an arylthio group having 6 to 10 carbon atoms that may have a substituent.

"a" represents an integer of from 0 to 5, and "b" represents an integer of from 0 to 5, provided that a+b=1 to 10, at least one of $R^1$ or $R^2$ represents the group having the radical-polymerizable group. As a matter of course, as long as at least one of $R^1$ or $R^2$ represents the group having the radical-polymerizable group, when a plurality of $R^1$s exist, $R^1$s may represent groups identical to or different from each other. In addition, the same holds true for $R^2$: when a plurality of $R^2$s exist, $R^2$s may represent groups identical to or different from each other.

Suitable examples of the alkyl group having 1 to 6 carbon atoms may include a methyl group, an ethyl group, a n-propyl group, an isopropyl group, a n-butyl group, a sec-butyl group, a tert-butyl group, a pentyl group, and a hexyl group.

The haloalkyl group having 1 to 6 carbon atoms is preferably an alkyl group substituted with a fluorine atom, a chlorine atom, or a bromine atom. Suitable examples of the haloalkyl group may include a trifluoromethyl group, a tetrafluoroethylgroup, a chloromethyl group, a 2-chloroethyl group, and a bromomethyl group.

Examples of the cycloalkyl group having 3 to 8 carbon atoms may include a cyclopropyl group, a cyclobutyl group, a cyclopentyl group, and a cyclohexyl group.

Suitable examples of the alkoxy group having 1 to 6 carbon atoms may include a methoxy group, an ethoxy group, a n-propoxy group, an isopropoxy group, a n-butoxy group, a sec-butoxy group, and a tert-butoxy group.

The amino group is not limited to a primary amino group (—$NH_2$), and may be a secondary or tertiary amino group obtained by substituting one or two hydrogen atoms of the primary amino group. Examples of the substituent of such amino group include an alkyl group having 1 to 6 carbon atoms, a haloalkyl group having 1 to 6 carbon atoms, an alkoxy group having 1 to 6 carbon atoms, a cycloalkyl group having 3 to 7 carbon atoms, an aryl group having 6 to 14 carbon atoms, and a heteroaryl group having 4 to 14 carbon atoms. Suitable examples of the amino group may include an amino group, a methylamino group, a dimethylamino group, an ethylamino group, a diethylamino group, a phenylamino group, and a diphenylamino group.

Preferred examples of the heterocyclic group may include: aliphatic heterocyclic groups, such as a morpholino group, a piperidino group, a pyrrolidinyl group, a piperazino group, and an N-methylpiperazino group; and aromatic heterocyclic groups, such as an indolinyl group. Further, the heterocyclic group may have a substituent. The substituent is preferably, for example, an alkyl group. Suitable examples of the heterocyclic group having a substituent include a 2,6-dimethylmorpholino group, a 2,6-dimethylpiperidino group, and a 2,2,6,6-tetramethylpiperidino group.

Examples of the halogen atom may include a fluorine atom, a chlorine atom, a bromine atom, and an iodine atom.

Examples of the alkylthio group having 1 to 6 carbon atoms may include a methylthio group, an ethylthio group, a n-propylthio group, an isopropylthio group, a n-butylthio group, a sec-butylthio group, and a t-butylthio group.

Examples of the arylthio group having 6 to 10 carbon atoms may include a phenylthio group, a 1-naphthylthio group, and a 2-naphthylthio group.

One to five hydrogen atoms, particularly preferably one to four hydrogen atoms of the aromatic ring of the arylthio group may each be substituted with an alkyl group having 1 to 6 carbon atoms, an alkoxy group having 1 to 6 carbon atoms, a cycloalkyl group having 3 to 8 carbon atoms, or a halogen atom. The number of carbon atoms of a substituent is not included in the number of carbon atoms of the arylthio group, that is, from 6 to 10.

From the viewpoint of the exhibition of an excellent photochromic characteristic, $R^1$ and $R^2$ each preferably represent a group selected from the alkyl group, the alkoxy group, the amino group, the substituted amino group, the heterocyclic group, and the halogen atom out of the foregoing groups as a group except the group having the radical-polymerizable group. Particularly suitable examples thereof include a methyl group, a methoxy group, a dimethylamino group, a morpholino group, a piperidino group, and a fluoro group.

As a particularly preferred group, the number of $R^1$s and $R^2$s each representing a group except the group having the radical-polymerizable group is preferably 1 or 0. In other words, each of the phenyl groups of the chromene compound is preferably in the state of being substituted with one group except the group having the radical-polymerizable group, or with no such group. When the phenyl group is substituted with one group, the phenyl group is preferably substituted with the group at its para position.

<$R^1$ and $R^2$; Group Having Radical-Polymerizable Group>

The group having the radical-polymerizable group is a group represented by the following formula (2).

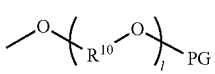

In the formula (2), $R^{10}$ represents a linear or branched alkylene group having 1 to 10 carbon atoms. Of those, an alkylene group having 1 to 5 carbon atoms is preferred. Suitable examples of the alkylene group having 1 to 5 carbon atoms may include a methylene group, an ethylene group, a n-propylene group, an isopropylene group, a n-butylene group, a sec-butylene group, a tert-butylene group, and a pentylene group.

"l" represents an integer of from 0 to 50. In consideration of the productivity of the chromene compound itself and an effect exhibited by the compound, "l" represents preferably an integer of from 1 to 20, more preferably an integer of from 1 to 10, still more preferably an integer of from 1 to 5, particularly preferably an integer of from 1 to 3, most preferably 1. In particular, to suppress the hydrolyzability of the chromene compound itself, "l" represents preferably an integer of from 1 to 5, more preferably an integer of from 1 to 3, still more preferably 1. When the hydrolysis of the chromene compound can be suppressed, a decomposed product of the chromene compound can be suppressed from bleeding out of a cured body, such as a photochromic contact lens. "l" represents the number of repeating units ($-R^{10}O-$). When "l" represents 2 or more, the unit groups (($-R^{10}O-$) groups) in "l" pairs of parentheses may be groups identical to or different from each other.

PG represents the radical-polymerizable group, and examples thereof include a vinyl group, a 1-chlorovinyl group, an allyl group, a styryl group, a (meth)acrylic group, a 2-(methacryloxy)ethylcarbamyl group, a 2-(methacryloxy) ethoxycarbonyl group, and a crotyl group. Of those, a (meth)acrylic group is most preferred in consideration of the productivity of the chromene compound itself and the performance of a photochromic optical article to be obtained.

<Numbers and Substitution Positions of $R^1$s and $R^2$s>

In the formula (1), "a" represents the number (substitution number) of $R^1$s and "b" represents the number (substitution number) of $R^2$s. In addition, "a" represents an integer of from 0 to 5, and "b" represents an integer of from 0 to 5, provided that a+b=1 to 10, and at least one of $R^1$ or $R^2$ represents the group having the radical-polymerizable group. In other words, as long as at least one of $R^1$ or $R^2$ represents the group having the radical-polymerizable group, the other symbols may each represent a group except the group having the radical-polymerizable group described in the section <$R^1$ and $R^2$> or a hydrogen atom.

The most preferred aspect out of those aspects is a case in which the number of the group having the radical-polymerizable group is 1. When the number of the group having the radical-polymerizable group is 2 or more, the elution of the photochromic compound can be suppressed, but the photochromic compound tends to be cross-linked to reduce its photochromic characteristic.

In addition, a position substituted with the group having the radical-polymerizable group is preferably the para position of each of the phenyl groups of 3,3-diphenylindenonaphthopyran. Accordingly, a preferred aspect is a case in which the para position of one of the phenyl groups is substituted with the group having the radical-polymerizable group. In this case, the other phenyl group is not limited, but of course, a case in which one substituent is present at its para position or no substituent is present thereat (a hydrogen atom is also present at the para position) is preferred. Of such cases, a case in which the other phenyl group is free of any substituent, or is substituted with the alkyl group, the alkoxy group, or the heterocyclic group at its para position is preferred.

<Ring Z (Group)>

A ring Z represented by the following formula (Z) (cyclic group being spiro-bonded to the carbon atom at the 13-position), the ring being spiro-bonded to a carbon atom at a 13-position of the indenonaphthopyran skeleton:

(Z)

is an aliphatic cyclic group that may have a substituent, the group having 3 to 20 carbon atoms for forming the ring together with the carbon atom at the 13-position, a condensed polycyclic group obtained by condensing the aliphatic cyclic group with an aromatic ring or an aromatic heterocycle that may have a substituent, a heterocyclic group that may have a substituent, the group having 3 to 20 atoms for forming the ring together with the carbon atom at the 13-position, or a condensed polycyclic group obtained by condensing the heterocyclic group with an aromatic ring or an aromatic heterocycle that may have a substituent. As a matter of course, the number of carbon atoms or the number of atoms described in each of the cyclic groups represents the number of carbon atoms, or atoms, for forming the ring, and does not include the number of carbon atoms, or atoms, of a substituent.

Examples of the aliphatic cyclic group include a cyclopentane ring group, a cyclohexane ring group, a cyclooctane ring group, a cycloheptane ring group, a norbornane ring group, a bicyclononane ring group, and an adamantane ring group.

In addition, an example of the condensed polycyclic group obtained by condensing the aliphatic cyclic group with an aromatic ring or an aromatic heterocycle is a phenanthrene ring group.

Examples of the heterocyclic group include a thiophene ring group, a furan ring group, and a pyridine ring group.

In addition, examples of the condensed polycyclic group obtained by condensing the heterocyclic group with an aromatic ring or an aromatic heterocycle include a phenylfuran ring group and a biphenylthiophene ring group.

The aliphatic cyclic group, the condensed polycyclic group obtained by condensing the aliphatic cyclic group with an aromatic ring or an aromatic heterocycle, the heterocyclic group, or the condensed polycyclic group obtained by condensing the heterocyclic group with an aromatic ring or an aromatic heterocycle may have a substituent. An example of the substituent substituting each of the cyclic groups (condensed polycyclic groups) is at least one kind of substituent selected from the group consisting of an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, and a halogen atom. Examples of the alkyl group, the haloalkyl group, the cycloalkyl group, the alkoxy group, the amino group, the substituted amino group, and the halogen atom include the same groups as the groups that have already been described in the section <$R^1$ and $R^2$>. Of the substituents of the ring Z, the alkyl group having 1 to 6 carbon atoms, the cycloalkyl group having 3 to 8 carbon atoms, the haloalkyl group having 1 to 6 carbon atoms, or the alkoxy group having 1 to 6 carbon atoms is particularly preferred as a substituent causing the chromene compound of the present invention to exhibit a particularly excellent effect.

In addition, the chromene compound of the present invention itself becomes a compound that is hardly hydrolyzed. For example, when the compound has a polymerizable group through an ester bond or an amide bond, such bond is liable to be hydrolyzed. Under such circumstances, the chromene compound of the present invention can suppress the hydrolysis. Although a reason for the foregoing is unclear, the suppression may result from the fact that the chromene compound of the present invention has the specific ring Z. When a compound free of the ring Z and the chromene compound of the present invention having the specific ring Z are compared to each other in the case where the compounds have the same group having the radical-polymerizable group, the chromene compound of the present invention becomes a bulky compound. Probably as a result of the foregoing, steric hindrance occurs in the chromene compound of the present invention to protect a moiety that is liable to be hydrolyzed. The effect becomes significant particularly when the compound has a (meth) acryl group, a 2-(methacryloxy)ethylcarbamyl group, or a 2-(methacryloxy) ethoxycarbonyl group. When the hydrolysis can be suppressed, a decomposed product of the chromene compound can be suppressed from bleeding out of a cured body, such as a photochromic contact lens.

Of the rings Z, to obtain a high color development density at around the surface temperature of an eye while securing a fast color fading rate, the aliphatic cyclic group having 5 to 16 carbon atoms for forming the ring, a cyclic group obtained by substituting such aliphatic cyclic group with an alkyl group having 1 to 6 carbon atoms (preferably an alkyl group having 1 to 3 carbon atoms), or a cyclic group obtained by bonding or condensing the aliphatic cyclic group with a cycloalkyl group having 3 to 8 carbon atoms is preferred.

A particularly suitable specific example of the ring Z is an unsubstituted cyclohexane ring group, cycloheptane ring group, cyclooctane ring group, cyclononane ring group, cyclodecane ring group, cycloundecane ring group, or cyclododecane ring group, each of which is free of any substituent.

In addition, the ring Z may be a cyclohexane ring group, but when the ring is the cyclohexane ring group, the cyclohexane ring group is substituted with preferably an alkyl group having 1 to 3 carbon atoms, more preferably an alkyl group having 1 or 2 carbon atoms. Further, in the case of the cyclohexane ring group substituted with the alkyl group, the substitution number of the alkyl groups is preferably from 1 to 10, more preferably from 2 to 6.

Further, in order that the effect through which the chromene compound has a high color development density even at around the surface temperature of an eye while having a fast color fading rate may be significant, the ring Z is preferably represented by any one of the following formulae.

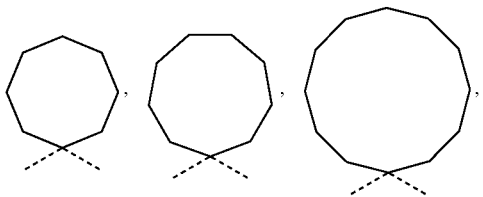

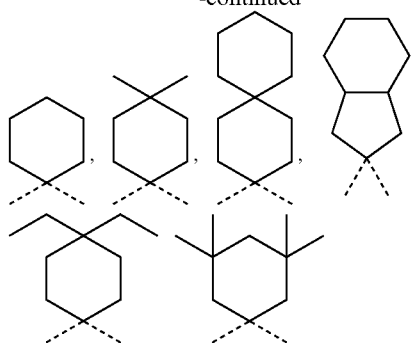

Further, when the ring Z is a group represented by any one of the formulae, the hydrolysis of the chromene compound itself can be further suppressed. This may result from the fact that the ring Z is bulky. When the hydrolysis can be suppressed, a decomposed product of the chromene compound can be suppressed from bleeding out of a cured body, such as a photochromic contact lens. In each of the formulae, a carbon atom having bonding hands represented by dotted lines is the carbon atom at the 13-position.

In addition, in order that in particular, the chromene compound can more significantly exhibit such effect that a high color development density is achieved at around the surface temperature of an eye, out of the cyclic groups, a group having 6 to 15 carbon atoms for forming the ring together with the carbon atom at the 13-position is preferred, and a group having 7 to 12 carbon atoms for forming the ring together with the carbon atom at the 13-position is more preferred.

Of the preferred cyclic groups, the cyclic group to be adopted for a case in which a chromene compound having a higher color development density is produced and the cyclic group to be adopted for a case in which a chromene compound having a faster color fading rate is produced are preferably different from each other.

That is, to obtain a chromene compound that has a higher color development density and is more useful even when used at high temperatures, a cyclic group represented by any one of the following formulae is preferably adopted.

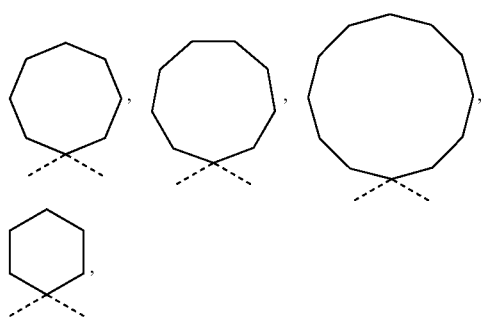

When such a cycloalkane ring having 6 to 12 carbon atoms (containing the carbon atom at the 13-position) as described above, the ring being free of any substituent, is adopted, a chromene compound having a particularly high color development density even when used at high temperatures is obtained.

Meanwhile, to obtain a chromene compound capable of responding at a higher speed (having a faster color fading rate), a cyclic group represented by any one of the following formulae is preferably adopted.

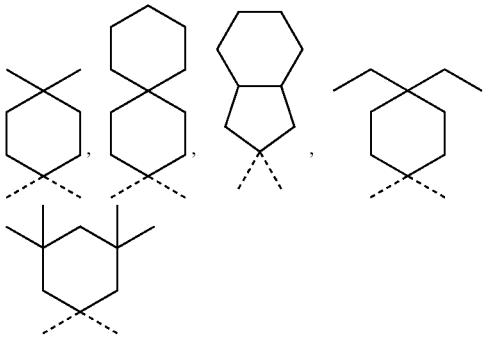

The adoption of such a group as described above can provide a chromene compound capable of responding at a higher speed.

<$R^3$>

$R^3$ represents a hydrogen atom, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, a cyano group, a halogen atom, an alkylthio group having 1 to 6 carbon atoms, an arylthio group having 6 to 10 carbon atoms that may have a substituent, a nitro group, a formyl group, a hydroxycarbonyl group, an alkylcarbonyl group having 2 to 7 carbon atoms, an alkoxycarbonyl group having 2 to 7 carbon atoms, an aralkyl group having 7 to 11 carbon atoms that may have a substituent, an aralkoxy group having 7 to 11 carbon atoms that may have a substituent, an aryloxy group having 6 to 12 carbon atoms that may have a substituent, an aryl group having 6 to 12 carbon atoms that may have a substituent, a heteroaryl group having 3 to 12 carbon atoms that may have a substituent, a thiol group, an alkoxyalkylthio group having 2 to 9 carbon atoms, a haloalkylthio group having 1 to 6 carbon atoms, or a cycloalkylthio group having 3 to 8 carbon atoms.

Examples of the alkyl group having 1 to 6 carbon atoms, the haloalkyl group having 1 to 6 carbon atoms, the cycloalkyl group having 3 to 8 carbon atoms, the alkoxy group having 1 to 6 carbon atoms, the halogen atom, the alkylthio group having 1 to 6 carbon atoms, or the arylthio group having 6 to 10 carbon atoms that may have a substituent out of the foregoing groups include the same groups as the groups described in the section <$R^1$ and $R^2$>, and preferred groups thereof are also the same.

Examples of the alkylcarbonyl group having 2 to 7 carbon atoms include an acetyl group and an ethylcarbonyl group.

Examples of the alkoxycarbonyl group having 2 to 7 carbon atoms include a methoxycarbonyl group and an ethoxycarbonyl group.

Examples of the aralkyl group having 7 to 11 carbon atoms may include a benzyl group, a phenylethyl group, a phenylpropyl group, a phenylbutyl group, and a naphthylmethyl group.

Examples of the aralkoxy group having 7 to 11 carbon atoms may include a benzyloxy group and a naphthylmethoxy group.

Examples of the aryloxy group having 6 to 12 carbon atoms may include a phenyloxy group and a naphthyloxy group.

Examples of the aryl group having 6 to 12 carbon atoms may include a phenyl group, a 1-naphthyl group, and a 2-naphthyl group.

Examples of the heteroaryl group having 3 to 12 carbon atoms may include a thienyl group, a furyl group, a pyrrolinyl group, a pyridyl group, a benzothienyl group, a benzofuranyl group, and a benzopyrrolinyl group.

Examples of the alkoxyalkylthio group having 2 to 9 carbon atoms may include a methoxymethylthio group, a methoxyethylthio group, a methoxy-n-propylthio group, a methoxy-n-butylthio group, an ethoxyethylthio group, and a n-propoxypropylthio group.

Examples of the haloalkylthio group having 1 to 6 carbon atoms may include a trifluoromethylthio group, a tetrafluoroethylthio group, a chloromethylthio group, a 2-chloroethylthio group, and a bromomethylthio group.

Examples of the cycloalkylthio group having 3 to 8 carbon atoms may include a cyclopropylthio group, a cyclobutylthio group, a cyclopentylthio group, and a cyclohexylthio group.

The aralkyl group, the aralkoxy group, the aryloxy group, the aryl group, and the heteroaryl group may each be unsubstituted. In addition, one to six hydrogen atoms, particularly preferably one to four hydrogen atoms of each of the groups may each be substituted with a substituent selected from a hydroxyl group, an alkyl group, a haloalkyl group, a cycloalkyl group, an alkoxy group, an amino group, a heterocyclic group, a cyano group, a nitro group, and a halogen atom. Examples of the substituent include the same groups as the groups described in the section <$R^1$ and $R^2$>. The number of carbon atoms limited in each of the aralkyl group, the aralkoxy group, the aryloxy group, the aryl group, and the heteroaryl group does not include the number of carbon atoms of a substituent.

<Particularly Suitable $R^3$>

In consideration of, for example, the developed color tone and color development density of a photochromic compound to be obtained, $R^3$ preferably represents a hydrogen atom, the alkyl group, the alkoxy group, the aryl group, or the arylthio group out of such groups as described above.

<$R^4$>

$R^4$ represents a hydrogen atom, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a heterocyclic group, a cyano group, a halogen atom, an alkylthio group having 1 to 6 carbon atoms, an arylthio group having 6 to 10 carbon atoms that may have a substituent, a nitro group, a formyl group, a hydroxycarbonyl group, an alkylcarbonyl group having 2 to 7 carbon atoms, an alkoxycarbonyl group having 2 to 7 carbon atoms, an aralkyl group having 7 to 11 carbon atoms that may have a substituent, an aralkoxy group having 7 to 11 carbon atoms that may have a substituent, an aryloxy group having 6 to 12 carbon atoms that may have a substituent, an aryl group having 6 to 12 carbon atoms that may have a substituent, a heteroaryl group having 3 to 12 carbon atoms that may have a substituent, a thiol group, an alkoxyalkylthio group having 2 to 9 carbon atoms, a haloalkylthio group having 1 to 6 carbon atoms, or a cycloalkylthio group having 3 to 8 carbon atoms.

Specific examples of the alkyl group having 1 to 6 carbon atoms, the haloalkyl group having 1 to 6 carbon atoms, the cycloalkyl group having 3 to 8 carbon atoms, the alkoxy group having 1 to 6 carbon atoms, the amino group, the heterocyclic group, the cyano group, the halogen atom, the alkylthio group having 1 to 6 carbon atoms, the arylthio group having 6 to 10 carbon atoms that may have a substituent, the alkylcarbonyl group having 2 to 7 carbon atoms, the alkoxycarbonyl group having 2 to 7 carbon atoms, the aralkyl group having 7 to 11 carbon atoms that may have a substituent, the aralkoxy group having 7 to 11 carbon atoms that may have a substituent, the aryloxy group having 6 to 12 carbon atoms that may have a substituent, the aryl group having 6 to 12 carbon atoms that may have a substituent, the heteroaryl group having 3 to 12 carbon atoms that may have a substituent, the alkoxyalkylthio group having 2 to 9 carbon atoms, the haloalkylthio group having 1 to 6 carbon atoms, or the cycloalkylthio group having 3 to 8 carbon atoms include specific groups listed in the section <$R^1$ and $R^2$> or the section <$R^3$>, and preferred groups thereof are also the same.

In addition, $R^3$ and $R^4$ may form a group represented by the following formula (3) together:

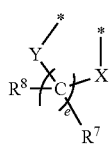

(3)

where * represents a carbon atom at a 6-position or a 7-position thereof.

In the formula, one, or each of both, of X and Y represents a sulfur atom, a methylene group, an oxygen atom, or a group represented by the following formula.

In the formula, $R^9$ represents a hydrogen atom, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an aryl group having 6 to 12 carbon atoms that may have a substituent, or a heteroaryl group having 3 to 12 carbon atoms that may have a substituent. Specific examples of those groups include specific groups listed in the section <$R^1$ and $R^2$> or the section <$R^3$>, and preferred groups thereof are also the same.

In addition, in the formula (3), $R^7$ and $R^8$ each independently represent a hydroxy group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group, a cyano group, a nitro group, a formyl group, a hydroxycarbonyl group, an alkylcarbonyl group having 2 to 7 carbon atoms, an alkoxycarbonyl group having 2 to 7 carbon atoms, a halogen atom, an aralkyl group having 7 to 11 carbon atoms that may have a substituent, an aralkoxy group having 7 to 11 carbon atoms that may have a substituent, an aryl group having 6 to 12 carbon atoms that may have a substituent, a thiol group, an alkylthio group having 1 to 6 carbon atoms, an alkoxyalkylthio group having 2 to 9 carbon atoms, a haloalkylthio group having 1 to 6 carbon atoms, a cycloalkylthio group having 3 to 8 carbon atoms, or an arylthio group having 6 to 10 carbon atoms that may have a substituent. Specific examples of those groups include specific groups listed in the section <$R^1$ and $R^2$> or the section <$R^3$>, and preferred groups thereof are also the same.

In addition, $R^7$ and $R^8$ may form an aliphatic ring together with a carbon atom to which $R^7$ and $R^8$ are bonded. Specific examples of the aliphatic ring include a cyclopentyl ring and a cyclohexyl ring.

In the formula, "e" represents an integer of from 1 to 3.

<Particularly Suitable $R^4$>

In consideration of, for example, the developed color tone and color development density of a photochromic compound to be obtained, $R^4$ preferably represents a hydrogen atom, the alkyl group, the alkoxy group, the heterocyclic group, the aryl group, or the arylthio group out of such groups as described above.

<$R^5$>

$R^5$ represents a hydroxy group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group, a cyano group, a nitro group, a formyl group, a hydroxycarbonyl group, an alkylcarbonyl group having 2 to 7 carbon atoms, an alkoxycarbonyl group having 2 to 7 carbon atoms, a halogen atom, an aralkyl group having 7 to 11 carbon atoms that may have a substituent, an aralkoxy group having 7 to 11 carbon atoms that may have a substituent, an aryl group having 6 to 12 carbon atoms that may have a substituent, a thiol group, an alkylthio group having 1 to 6 carbon atoms, an alkoxyalkylthio group having 2 to 9 carbon atoms, a haloalkylthio group having 1 to 6 carbon atoms, a cycloalkylthio group having 3 to 8 carbon atoms, or an arylthio group having 6 to 10 carbon atoms that may have a substituent.

"c" represents an integer of from 0 to 2, and when "c" represents 2, $R^5$s may represent groups identical to or different from each other.

Specific examples of the alkyl group having 1 to 6 carbon atoms, the haloalkyl group having 1 to 6 carbon atoms, the cycloalkyl group having 3 to 8 carbon atoms, the alkoxy group having 1 to 6 carbon atoms, the amino group, the heterocyclic group, the alkylcarbonyl group having 2 to 7 carbon atoms, the alkoxycarbonyl group having 2 to 7 carbon atoms, the halogen atom, the aralkyl group having 7 to 11 carbon atoms that may have a substituent, the aralkoxy group having 7 to 11 carbon atoms that may have a substituent, the aryl group having 6 to 12 carbon atoms that may have a substituent, the thiol group, the alkylthio group having 1 to 6 carbon atoms, the alkoxyalkylthio group having 2 to 9 carbon atoms, the haloalkylthio group having 1 to 6 carbon atoms, the cycloalkylthio group having 3 to 8 carbon atoms, or the arylthio group having 6 to 10 carbon atoms that may have a substituent include specific groups listed in the section <$R^1$ and $R^2$> or the section <$R^3$> and the section <$R^4$>, and preferred groups thereof are also the same.

<Particularly Suitable $R^3$>

In consideration of, for example, the developed color tone and color development density of a photochromic compound to be obtained, $R^5$ preferably represents a hydrogen atom or the alkoxy group out of such groups as described above.

<$R^6$>

$R^6$ represents a hydroxy group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group, a halogen atom, an aralkyl group having 7 to 11 carbon atoms that may have a substituent, an aralkoxy group having 7 to 11 carbon atoms that may have a substituent, a thiol group, an alkylthio group having 1 to 6 carbon atoms, an alkoxyalkylthio group having 2 to 9 carbon atoms, a haloalkylthio group having 1 to 6 carbon atoms, a cycloalkylthio group having 3 to 8 carbon atoms, or an arylthio group having 6 to 10 carbon atoms that may have a substituent.

"d" represents an integer of from 0 to 4, and when "d" represents 2 or more, $R^6$s may represent groups identical to or different from each other.

Specific examples of the alkyl group having 1 to 6 carbon atoms, the haloalkyl group having 1 to 6 carbon atoms, the cycloalkyl group having 3 to 8 carbon atoms, the alkoxy group having 1 to 6 carbon atoms, the amino group, the heterocyclic group, the halogen atom, the aralkyl group having 7 to 11 carbon atoms that may have a substituent, the aralkoxy group having 7 to 11 carbon atoms that may have a substituent, the thiol group, the alkylthio group having 1 to 6 carbon atoms, the alkoxyalkylthio group having 2 to 9 carbon atoms, the haloalkylthio group having 1 to 6 carbon atoms, the cycloalkylthio group having 3 to 8 carbon atoms, or the arylthio group having 6 to 10 carbon atoms that may have a substituent include specific groups listed in the section <$R^1$ and $R^2$>, the section <$R^3$>, or the section <$R^4$>, and the section <$R^3$>, and preferred groups thereof are also the same.

<Particularly Suitable $R^6$>

In consideration of, for example, the developed color tone and color development density of a photochromic compound to be obtained, $R^6$ preferably represents a hydrogen atom or the alkoxy group out of such groups as described above.

<Particularly Suitable Chromene Compound>

Specific examples of a particularly suitable chromene compound in the present invention include chromene compounds represented by the following formulae.

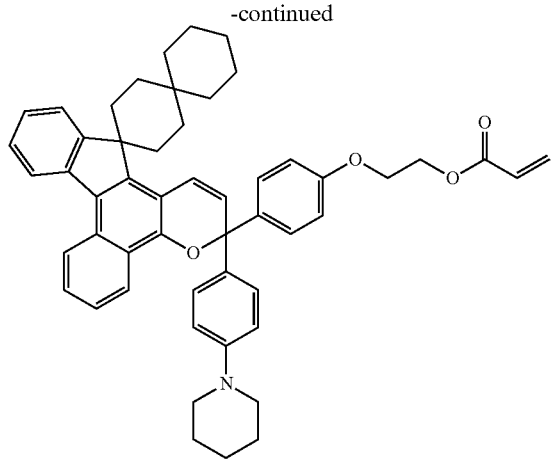

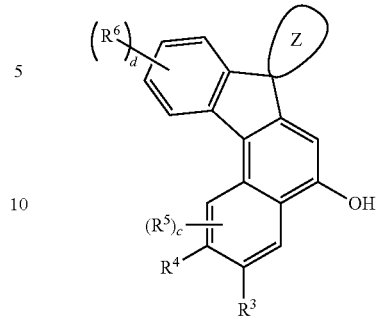

(10)

and a propargyl alcohol compound represented by the following formula (11) to react with each other in the presence of an acid catalyst.

<Identification of Chromene Compound>

The chromene compound of the present invention generally exists as a colorless, pale yellow, or pale green solid or viscous liquid at normal temperature and normal pressure, and can be identified by the following methods (a) to (c).

(a) When the proton nuclear magnetic resonance spectrum ($^1$H-NMR) of the chromene compound is measured, a peak based on an aromatic proton and the proton of an alkene appears at a δ of from about 5.0 ppm to about 9.0 ppm, and a peak based on the protons of an alkyl group and an alkylene group appears at a δ of from about 1.0 ppm to about 4.0 ppm. In addition, the number of protons of each bonding group can be understood by relatively comparing the spectral intensities of the respective peaks.

(b) The composition of a corresponding product can be determined by elemental analysis.

(c) When the $^{13}$C nuclear magnetic resonance spectrum ($^{13}$C-NMR) of the chromene compound is measured, a peak based on the carbon atoms of an aromatic hydrocarbon group appears at a δ of from about 110 ppm to about 160 ppm, a peak based on the carbon atoms of an alkene and an alkyne appears at a δ of from about 80 ppm to about 140 ppm, and a peak based on the carbon atoms of an alkyl group and an alkylene group appears at a δ of from about 20 ppm to about 80 ppm.

<Production of Chromene Compound>

The chromene compound of the present invention may be produced by any synthesis method. An example of a suitable method of producing the chromene compound is described. In the following description, the symbols in the respective formulae each represent the same meaning as that described for the above-mentioned formulae unless otherwise stated.

The chromene compound can be suitably produced by a method including causing a naphthol compound represented by the following formula (10):

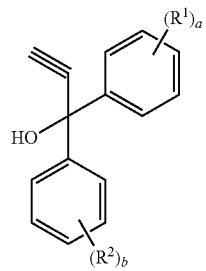

(11)

A reaction ratio between the naphthol compound and the propargyl alcohol compound is preferably selected from the range of from 1:10 to 10:1 (molar ratio). In addition, for example, sulfuric acid, benzenesulfonic acid, p-toluenesulfonic acid, or acidic alumina is used as the acid catalyst. The acid catalyst is preferably used in an amount in the range of from 0.1 part by weight to 10 parts by weight per 100 parts by weight of the sum of the naphthol compound and the propargyl alcohol compound. A reaction temperature is preferably from 0° C. to 200° C. An aprotic organic solvent, such as N-methylpyrrolidone, dimethylformamide, tetrahydrofuran, benzene, or toluene, is preferably used as a solvent. A method of purifying the product obtained by such reaction is not particularly limited. For example, the product may be purified by purifying the product with a silica gel column and recrystallizing the purified product.

Of the naphthol compounds each represented by the formula (10), a compound having a structure enabling the production of a preferred chromene compound represented by the formula (1) is a preferred compound. For example, compounds represented by the following formulae may be listed as particularly preferred compounds.

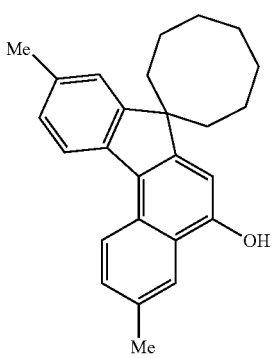
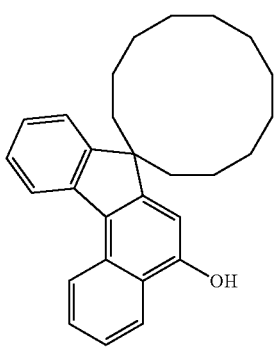
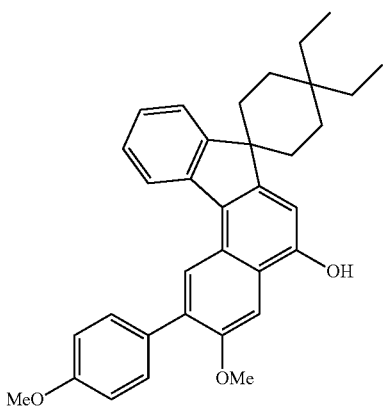
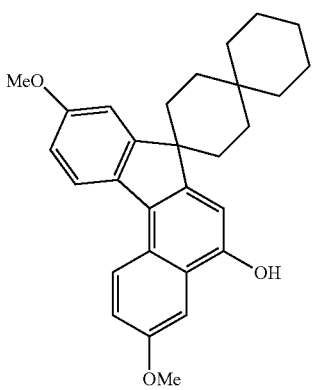
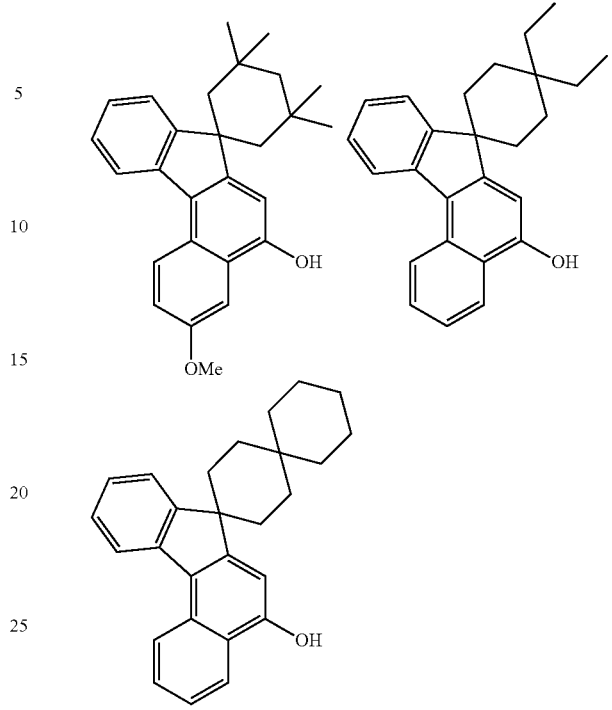

The naphthol compound represented by the formula (10) may be synthesized, for example, as described below. The naphthol compound can be synthesized on the basis of a reaction method described in a thesis, such as WO 2001/60881 A2 or WO 2005/028465 A1. Specifically, the naphthol compound can be produced by the following method.

First, a benzophenone compound represented by the following formula (12):

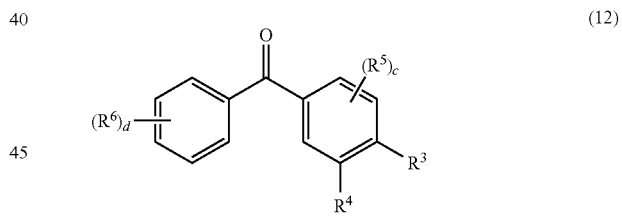

(12)

is subjected to a Stobbe reaction and a cyclization reaction to provide a compound represented by the following formula (13).

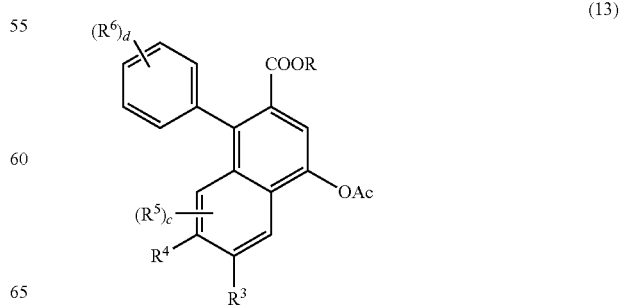

(13)

In the compound represented by the formula (13), R represents a group derived from a diester compound used in the Stobbe reaction, and Ac represents an acetyl group. Next, the compound (13) is hydrolyzed with an alkali or an acid to provide a carboxylic acid represented by the following formula (14).

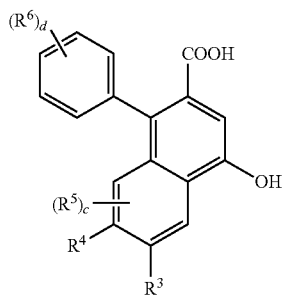

(14)

The carboxylic acid is subjected to benzylation with a base, such as potassium carbonate, and benzyl chloride, and is then hydrolyzed with an alkali or an acid to provide a benzyl-protected carboxylic acid represented by the following formula (15):

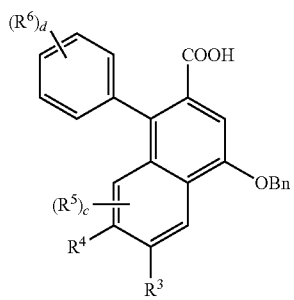

(15)

(in the formula (15), Bn represents a benzyl group). The benzyl-protected carboxylic acid is converted into an amine by a method, such as Curtius rearrangement, Hofmann rearrangement, or Lossen rearrangement, and a diazonium salt is prepared from the amine by a method known per se. The diazonium salt is converted into a bromide by a Sandmeyer reaction or the like, and the resultant bromide is caused to react with magnesium, lithium, or the like to prepare an organometallic compound. The organometallic compound is caused to react with a ketone represented by the following formula (16):

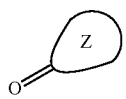

(16)

in an organic solvent at from −80° C. to 70° C. for from 10 minutes to 4 hours, and then the resultant is subjected to a debenzylation reaction with hydrogen and palladium carbon or the like to provide an alcohol represented by the following formula (17).

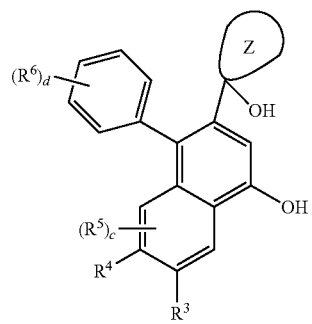

(17)

The alcohol is subjected to a Friedel-Crafts reaction under a neutral to acidic condition at from 10° C. to 120° C. for from 10 minutes to 2 hours. Thus, the target naphthol compound represented by the formula (10) can be synthesized. In such reaction, a reaction ratio between the organometallic compound and the ketone represented by the formula (16) is preferably selected from the range of from 1:10 to 10:1 (molar ratio). A reaction temperature is preferably from −80° C. to 70° C. An aprotic organic solvent, such as diethyl ether, tetrahydrofuran, benzene, or toluene, is preferably used as the solvent. In addition, the Friedel-Crafts reaction of the alcohol represented by the formula (17) under the neutral to acidic condition is preferably performed by using an acid catalyst, such as acetic acid, hydrochloric acid, sulfuric acid, benzenesulfonic acid, p-toluenesulfonic acid, or acidic alumina. Such acid catalyst is suitably used in an amount in the range of from 0.1 part by weight to 10 parts by weight per 100 parts by weight of the alcohol represented by the formula (17). An aprotic organic solvent, such as tetrahydrofuran, benzene, or toluene, is used at the time of the reaction.

Meanwhile, the propargyl alcohol compound represented by the formula (11) may be easily synthesized by, for example, causing a ketone compound corresponding to the formula (11) and a metal acetylene compound, such as lithium acetylide, to react with each other. When the polymerizable group is introduced into the propargyl alcohol compound represented by the formula (11) by a known method, the chromene compound of the present invention can be produced by performing the reaction between the propargyl alcohol compound and the naphthol compound represented by the formula (10).

Although the chromene compound of the present invention can be produced by such method as described above, to further simplify the reactions and to suppress a by-product, the radical-polymerizable group is preferably introduced as described below. Specifically, the position of the propargyl alcohol compound into which the radical-polymerizable group is wished to be introduced is substituted with a reactive substituent, such as a hydroxyl group, a primary or secondary amino group, a thiol group, or a hydrosilyl group, in advance. Next, the propargyl alcohol compound having the reactive substituent and the naphthol compound represented by the formula (10) are caused to react with each other in accordance with the foregoing method to produce a precursor of the chromene compound of the present invention. Then, the radical-polymerizable group is introduced into the reactive substituent of the resultant precursor to produce the chromene compound of the present invention.

A known method may be adopted as a method of introducing the radical-polymerizable group into the reactive substituent.

For example, when a (meth) acrylic group is introduced as the radical-polymerizable group, a precursor having a hydroxyl group as the reactive substituent and (meth) acryloyl chloride only need to be caused to react with each other in the presence of a basic catalyst. In addition to the foregoing, the radical-polymerizable group can be introduced by causing a precursor having an amino group or a hydroxyl group and 2-isocyanatoethyl (meth)acrylate to react with each other. In addition, the radical-polymerizable group can be introduced by hydrosilylating a precursor having a hydrosilyl group as the reactive substituent and allyl methacrylate through use of chloroplatinic acid as a catalyst.

In addition, when a vinyl group is introduced as the radical-polymerizable group, the radical-polymerizable group can be introduced by causing a precursor having a hydroxyl group as the reactive substituent and vinyl chloride or allyl bromide to react with each other.

When the radical-polymerizable group is a styryl group, the radical-polymerizable group can be introduced by hydrosilylating a precursor having a hydrosilyl group as the reactive substituent and divinylbenzene in the presence of a chloroplatinic acid catalyst.

A more specific example of the production method is described below. For example, a method of synthesizing a precursor having a hydroxyl group as the reactive substituent and a conversion scheme when an acrylic group is introduced as the radical-polymerizable group into the precursor are described below.

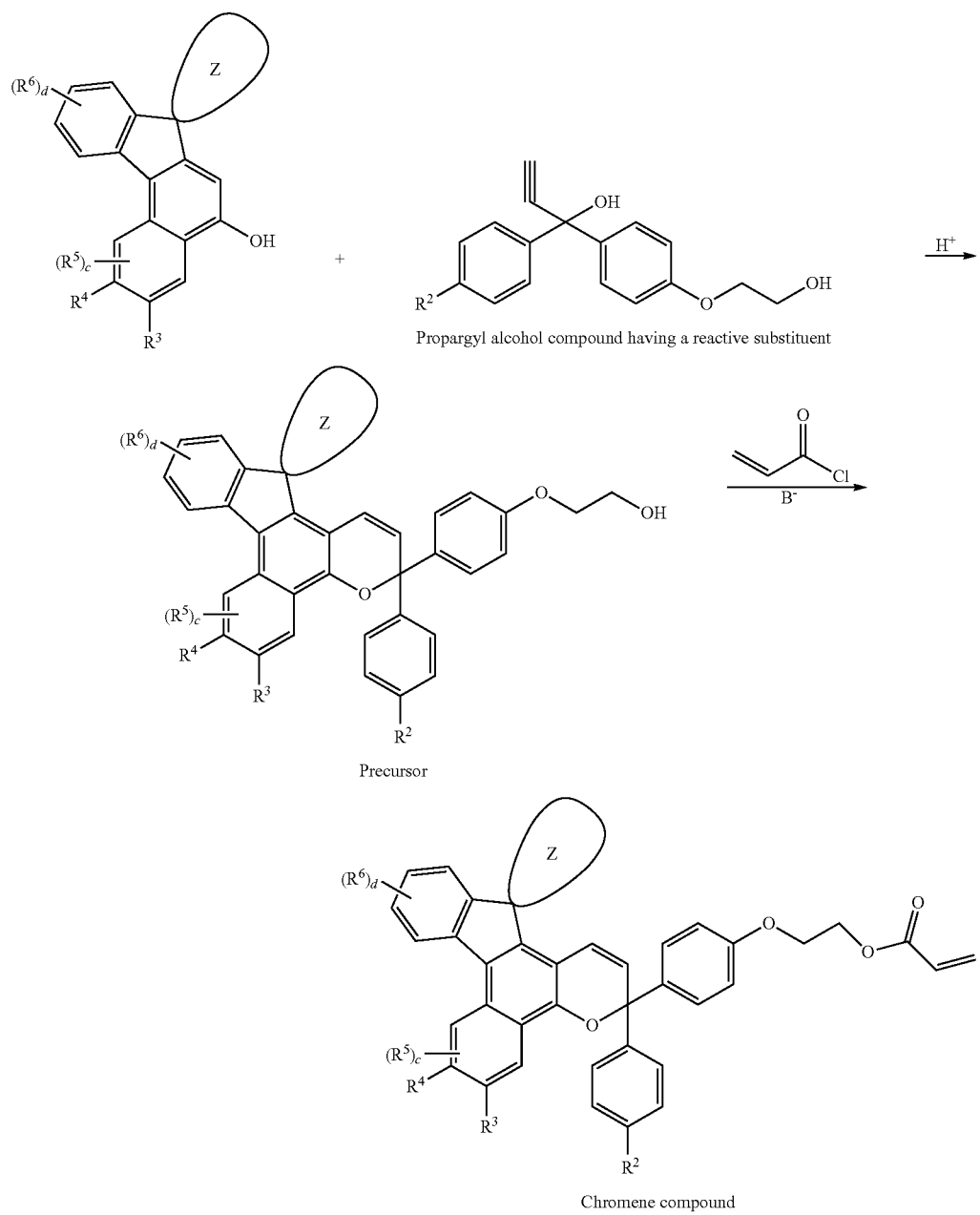

The precursor having a hydroxyl group can be obtained by causing the naphthol compound represented by the formula (10) and a propargyl alcohol compound having a hydroxyl group as the reactive substituent to react with each other under an acidic condition. The chromene compound is obtained by causing the precursor to react with acryloyl chloride in the presence of a basic catalyst, such as a tertiary amine.

<Combination with any Other Photochromic Compound (Photochromic Composition)>

The chromene compound of the present invention is dissolved well in a general organic solvent, such as toluene, chloroform, or tetrahydrofuran. When the chromene compound represented by the formula (1) is dissolved in such solvent, in general, the solution is substantially colorless and transparent, and shows the following satisfactory photochromic action: when the solution is irradiated with sunlight or UV light, the solution immediately develops a color, and when the light is blocked, the solution immediately returns to its original state, that is, a colorless state in a reversible manner. In addition, the chromene compound of the present invention may be used in combination with any other photochromic compound in accordance with target applications. For example, the compound may be used in combination with the other photochromic compound for obtaining various color tones required as a photochromic lens. A known photochromic compound may be used as the photochromic compound to be combined without any limitation. Examples thereof include a fulgide, a fulgimide, a spirooxazine, and a chromene compound. Of those, a chromene compound is particularly preferred because of the following reasons: the color tone of a photochromic composition can be kept uniform during a time period from the color development thereof to the color fading thereof; the color shift thereof at the time of the color development along with the deterioration of the photochromic property thereof can be suppressed; and the initial coloring thereof can be reduced. However, when the photochromic composition is used for a contact lens, the other photochromic compound also preferably has a radical-polymerizable group. Alternatively, the color tone of the contact lens is preferably adjusted by using the plurality of kinds of chromene compounds of the present invention.

When a photochromic composition containing the chromene compound of the present invention and the other chromene compound is produced, the blending ratios of the respective chromene compounds are appropriately determined in accordance with a desired color tone.

The chromene compound of the present invention has the radical-polymerizable group, and hence the homopolymerization thereof can provide an optical article. However, in order that the compound may be used in various applications, the compound is preferably used as the following aspect.

<Photochromic Curable Composition>

The chromene compound of the present invention and the photochromic composition are each preferably used as a photochromic curable composition in combination with a polymerizable monomer except the chromene compound (hereinafter sometimes simply referred to as "other polymerizable monomer").

In the present invention, the photochromic curable composition preferably adopts the following blending ratio, though the ratio depends on the color development intensity of the chromene compound, a selected lens material, and the thickness of a lens, and hence cannot be unconditionally determined. Specifically, the chromene compound of the present invention or the photochromic composition is preferably used in an amount of from 0.001 part by mass to 10 parts by mass with respect to 100 parts by mass of the other polymerizable monomer. The blending amount is preferably adjusted to an optimum blending amount in accordance with an application where the photochromic curable composition is used. For example, when the photochromic curable composition is used as a thin-film optical article, and when the photochromic curable composition is used as a thick-film optical article, the blending amount is adjusted as described below.

Specifically, when the photochromic curable composition is turned into a thin film like a coating, for example, a thin film having a thickness of about 100 μm (polymer film obtained by polymerizing the photochromic curable composition), the color tone of the thin film is desirably adjusted by setting the amount of the chromene compound of the present invention or the photochromic composition to from 0.001 part by mass to 10 parts by mass with respect to 100 parts by mass of the other polymerizable monomer.

In the case of a thick cured body (polymer molded body obtained by polymerizing the photochromic curable composition), for example, a cured body having a thickness of 1 mm or more, its color tone is desirably adjusted by setting the amount of the chromene compound of the present invention or the photochromic composition to from 0.001 part by mass to 1 part by mass with respect to 100 parts by mass of the thick cured body or the other polymerizable monomer that provides the thick cured body.

In addition, when the photochromic curable composition is used for a contact lens, the following formulation is preferably adopted. That is, the chromene compound of the present invention or the photochromic composition is preferably used in an amount of from 0.001 part by mass to 5 parts by mass with respect to 100 parts by mass of the other polymerizable monomer.

<Other Polymerizable Monomer>

The other polymerizable monomer to be used in the present invention is not particularly limited as long as the monomer can be copolymerized with the chromene compound of the present invention by radical polymerization. Radical-polymerizable compounds are roughly classified into a (meth)acrylic polymerizable compound having a (meth)acrylic group, a vinyl-based polymerizable compound having a vinyl group, an allyl-based polymerizable compound having an allyl group, and a silsesquioxane-based polymerizable compound.

Specific examples thereof are described below.

<(Meth)Acrylic Polymerizable Compound Having (Meth)Acrylic Group>

Examples of a polyfunctional (meth)acrylic polymerizable compound having a (meth)acrylic group include the following polymerizable compounds. Specific examples thereof include:

glycol-based difunctional (meth)acrylic polymerizable compounds selected from diethylene glycol dimethacrylate, triethylene glycol dimethacrylate, tetraethylene glycol dimethacrylate, pentaethylene glycol dimethacrylate, pentapropylene glycol dimethacrylate, diethylene glycol diacrylate, triethylene glycol diacrylate, tetraethylene glycol diacrylate, pentaethylene glycol diacrylate, tripropylene glycol diacrylate, tetrapropylene glycol diacrylate, pentapropylene glycol diacrylate, dimethacrylate formed of a mixture of polypropylene glycol and polyethylene glycol (having a repeating unit of two polyethylenes and two polypropylenes), polyethylene glycol dimethacrylate (in particular, average molecular weight: 330), polyethylene glycol dimethacrylate (in particular, average molecular weight: 536), polyethylene glycol dimethacrylate (in particular, average molecular weight: 736), tripropylene glycol dimethacrylate, tetrapropylene glycol dimethacrylate, polypropylene glycol dimethacrylate (in particular, average molecular weight: 536), polyethylene glycol diacrylate (in particular, average molecular weight: 258), polyethylene glycol diacrylate (in particular, average molecular weight: 308), polyethylene glycol diacrylate (in particular, average molecular weight: 508), polyethylene glycol diacrylate (in particular, average molecular weight: 708), and polyethylene glycol methacrylate acrylate (in particular, average molecular weight: 536);

polyalkylene glycol (meth)acrylates, such as trimethylolpropane trimethacrylate, trimethylolpropane triacrylate, tetramethylolmethane trimethacrylate, tetramethylolmethane triacrylate, tetramethylolmethane tetramethacrylate, tetramethylolmethane tetraacrylate, trimethylolpropane triethylene glycol trimethacrylate, trimethylolpropane triethylene glycol triacrylate, ditrimethylolpropane tetramethacrylate, and ditrimethylolpropane tetraacrylate;

bisphenol A (meth)acrylates, such as 2,2-bis[4-methacryloyloxyethoxy)phenyl]propane, 2,2-bis[4-methacryloyloxydiethoxy)phenyl]propane, 2,2-bis[4-methacryloyloxypolyethoxy)phenyl]propane, 2,2-bis(3,5-dibromo-4-methacryloyloxyethoxyphenyl)propane, 2,2-bis(4-methacryloyloxydipropoxyphenyl)propane, 2,2-bis[4-acryloyloxydiethoxy)phenyl]propane, 2,2-bis[4-acryloyloxy(polyethoxy)phenyl]propane, and 2,2-bis[4-methacryloyloxy(polyethoxy)phenyl]propane;

(meth)acrylates of a polycarbonate diol, such as a reaction product of a polycarbonate diol (having a number average molecular weight of from 500 to 2,000) obtained by phosgenation of apolyalkylene glycol, such as trimethylene glycol, tetramethylene glycol, pentamethylene glycol, hexamethylene glycol, octamethylene glycol, or nonamethylene glycol, and (meth)acrylic acid, a reaction product of a polycarbonate diol (number average molecular weight: 500 to 2,000) obtained by phosgenation of a mixture of two or more kinds of polyalkylene glycols (e.g., a mixture of trimethylene glycol and tetramethylene glycol, a mixture of tetramethylene glycol and hexamethylene diglycol, a mixture of pentamethylene glycol and hexamethylene glycol, a mixture of tetramethylene glycol and octamethylene glycol, or a mixture of hexamethylene glycol and octamethylene glycol), and (meth) acrylic acid, and a reaction product of a polycarbonate diol (number average molecular weight: 500 to 2,000) obtained by phosgenation of 1-methyltrimethylene glycol, and (meth)acrylic acid;

(meth)acrylates each having a urethane bond, such as U-2PPA (molecular weight: 482), UA-122P (molecular weight: 1,100), U-122P (molecular weight: 1,100), U-108A, U-200PA, UA-511, U-412A, UA-4100, UA-4200, UA-4400, UA-2235PE, UA-160TM, UA-6100, UA-6200, U-108, UA-4000, and UA-512 manufactured by Shin-Nakamura Chemical Co., Ltd., EB4858 (molecular weight: 454) manufactured by Daicel-UCB Company, UX-2201, UX3204, UX4101, 6101, 7101, and 8101 manufactured by Nippon Kayaku Co., Ltd., and U-4HA (molecular weight: 596, number of functional groups: 4), U-6HA (molecular weight: 1,019, number of functional groups: 6), U-6LPA (molecular weight: 818, number of functional groups: 6), and U-15HA (molecular weight: 2,300, number of functional groups: 15) manufactured by Shin-Nakamura Chemical Co., Ltd.;

alkyldiol di(meth)acrylates, such as 1,6-hexanediol diacrylate, 1,6-hexanediol dimethacrylate, 1,9-nonanediol diacrylate, 1,9-nonanediol dimethacrylate, 1,10-decanediol diacrylate, and 1,10-decanediol dimethacrylate;

sulfur atom-containing (meth)acrylates, such as bis(2-methacryloyloxyethylthioethyl) sulfide, bis(methacryloyloxyethyl) sulfide, bis(acryloyloxyethyl) sulfide, 1,2-bis(methacryloyloxyethylthio)ethane, 1,2-bis(acryloyloxyethyl)ethane, bis(2-methacryloyloxyethylthioethyl) sulfide, bis(2-acryloyloxyethylthioethyl) sulfide, 1,2-bis(methacryloyloxyethylthioethylthio)ethane, 1,2-bis(acryloyloxyethylthioethylthio)ethane, 1,2-bis(methacryloyloxyisopropylthioisopropyl) sulfide, and 1,2-bis(acryloyloxyisopropylthioisopropyl) sulfide; and polyester (meth)acrylates, such as a tetrafunctional polyester oligomer (e.g., molecular weight: 2,500 to 3,500, Daicel-UCB Company, EB80), a hexafunctional polyester oligomer (e.g., molecular weight: 6,000 to 8,000, Daicel-UCB Company, EB450), a hexafunctional polyester oligomer (e.g., molecular weight: 45,000 to 55,000, Daicel-UCB Company, EB1830), and a tetrafunctional polyester oligomer (in particular, for example, GX8488B manufactured by DKS Co., Ltd., molecular weight: 10,000).

In addition, examples of a monofunctional (meth)acrylic polymerizable compound having a (meth)acrylic group include methoxypolyethylene glycol methacrylate (in particular, average molecular weight: 293), methoxypolyethylene glycol methacrylate (in particular, average molecular weight: 468), methoxypolyethylene glycol acrylate (in particular, average molecular weight: 218), methoxypolyethylene glycol acrylate (in particular, average molecular weight: 454), stearyl methacrylate, lauryl methacrylate, methyl acrylate, ethyl acrylate, butyl acrylate, octyl acrylate, lauryl acrylate, γ-methacryloyloxypropyltrimethoxysilane, γ-methacryloyloxypropylmethyldimethoxysilane, and glycidyl methacrylate.

<Vinyl-Based Polymerizable Compound Having Vinyl Group>

Examples of the vinyl-based polymerizable compound include the following compounds. Specific examples thereof include methyl vinyl ketone, ethyl vinyl ketone, ethyl vinyl ether, styrene, vinylcyclohexane, butadiene, 1,4-pentadiene, divinyl sulfide, divinylsulfone, 1,2-divinylbenzene, 1,3-divinyl-1,1,3,3-tetramethylpropanedisiloxane, diethylene glycol divinyl ether, divinyl adipate, divinyl sebacate, ethylene glycol divinyl ether, divinyl sulfoxide, divinyl persulfide, dimethyldivinylsilane, 1,2,4-trivinylcyclohexane, methyltrivinylsilane, α-methylstyrene, and α-methylstyrene dimer.

Of the vinyl-based polymerizable compounds listed above, each of α-methylstyrene and α-methylstyrene dimer functions as a polymerization modifier to improve the moldability of the photochromic curable composition.

<Allyl-Based Polymerizable Compound Having Allyl Group>

Examples of the allyl-based polymerizable compound include diethylene glycol bisallyl carbonate, methoxypolyethylene glycol allyl ether (in particular, average molecular weight: 550), methoxypolyethylene glycol allyl ether (in particular, average molecular weight: 350), methoxypolyethylene glycol allyl ether (in particular, average molecular weight: 1,500), polyethylene glycol allyl ether (in particular, average molecular weight: 450), methoxypolyethylene glycol-polypropylene glycol allyl ether (in particular, average molecular weight: 750), butoxypolyethylene glycol-polypropylene glycol allyl ether (in particular, average molecular weight: 1,600), methacryloyloxypolyethylene glycol-polypropylene glycol allyl ether (in particular, average molecular weight: 560), phenoxypolyethylene glycol allyl ether (in particular, average molecular weight: 600), methacryloyloxypolyethylene glycol allyl ether (in particular, average molecular weight: 430), acryloyloxypolyethylene glycol allyl ether (in particular, average molecular weight: 420), vinyloxypolyethylene glycol allyl ether (in particular, average molecular weight: 560), styryloxypolyethylene glycol allyl ether (in particular, average molecular weight: 650), and methoxypolyethylene thioglycol allyl thioether (in particular, average molecular weight: 730).

The allyl-based polymerizable compound can act as a chain transfer agent to improve the photochromic properties (color development density and color fading rate) of the curable composition.

<Silsesquioxane-Based Polymerizable Compound>

The silsesquioxane-based polymerizable compound adopts various molecular structures, such as a cage-like structure, a ladder-like structure, and a random structure, and has a radical-polymerizable group, such as a (meth)acrylic group. An example of such silsesquioxane-based polymerizable compound is a compound represented by the following formula (18):

$$R^{12}\text{—}(SiO_{3/2})_s \qquad (18)$$

where "s" represents a polymerization degree, and represents an integer of from 3 to 100, and a plurality of $R^{12}$s may be identical to or different from each other, and each represent a radical-polymerizable group, an organic group including a radical-polymerizable group, a hydrogen atom, an alkyl group, a cycloalkyl group, an alkoxy group, or a phenyl group, and at least one of $R^{12}$s represents a radical-polymerizable group or an organic group including a radical-polymerizable group.

Herein, examples of the radical-polymerizable group or the organic group including the radical-polymerizable group represented by $R^{12}$ include: a (meth)acrylic group; organic groups each having a (meth)acrylic group, such as a (meth)acryloyloxypropyl group and a (3-(meth)acryloyloxypropyl) dimethylsiloxy group; an allyl group; organic groups each having an allyl group, such as an allylpropyl group and an allylpropyldimethylsiloxy group; a vinyl group; and organic groups each having a vinyl group, such as a vinylpropyl group and a vinyldimethylsiloxy group.

In addition, when the chromene compound of the present invention is used in a contact lens application, the compound is preferably combined with a radical-polymerizable monomer to be described below in addition to the radical-polymerizable polyfunctional monomers and the radical-polymerizable monofunctional monomers described above. That is, a contact lens having dispersed therein the chromene compound of the present invention is preferably produced by copolymerizing the other polymerizable monomer to be described in detail below and the chromene compound of the present invention.

<Contact Lens Application; Other Polymerizable Monomer>

When a hard contact lens, a soft contact lens, or a silicone hydrogel soft contact lens is produced by using the chromene compound of the present invention, a contact lens having an excellent photochromic characteristic can be produced. The compound shows a particularly excellent photochromic characteristic in a soft contact lens containing a hydrogel or a silicone hydrogel out of such contact lenses. The hydrogel refers to a substance obtained by the swelling of a polymer having a three-dimensional network structure as a result of its water absorption, and the silicone hydrogel refers to a substance in which a silicone component is used in a monomer for forming a hydrogel. The water content of each of the hydrogel and the silicone hydrogel, which is not particularly limited, is typically from 20 mass % to 80 mass %.

When the chromene compound of the present invention is used as a monomer for a contact lens, the compound is preferably combined with a hydrophilic monomer to provide a photochromic curable composition. The hydrophilic monomer refers to a monomer having at least one of a hydroxy group, an amino group, an amide group, an ether group, cyclic nitrogen, or a carboxyl group in a molecule thereof.

In the present invention, specific examples of the hydrophilic monomer include:

hydroxyalkyl (meth)acrylates, such as 2-hydroxyethyl (meth)acrylate, hydroxypropyl (meth)acrylate, and glycerol methacrylate; and aminoalkyl (meth)acrylates, such as aminoethyl (meth)acrylate, dimethylaminoethyl (meth)acrylate, methylaminoethyl (meth)acrylate, and diethylaminoethyl acrylate.

The examples also include N-vinyl compounds, such as N-vinylpyrrolidone, N-vinylpiperidone, N-vinyl-N-methylacetamide, N-vinyl-N-ethylacetamide, N-vinyl-N-ethylformamide, N-vinylpyrrolidinone, N-vinylformamide, N-2-hydroxyethyl vinyl carbamate, N-vinylpyridine, and N-vinylglutarimide, N-vinylsuccinimide, and N-vinyl-ε-caprolactam.

The examples also include amide derivatives of (meth) acrylic acid, such as N-methyl(meth)acrylamide, N-isopropyl(meth)acrylamide, N-diacetone (meth)acrylamide, N,N-dimethylacrylamide, N,N-dimethylamino-methyl(meth) acrylamide, N,N-dimethylaminoethyl(meth)acrylamide, N,N-diethyl(meth)acrylamide, acryloylmorpholine, N,N-dipropyl(meth)acrylamide, N-methylaminoisopropyl(meth) acrylamide, and N-(2-hydroxyethyl) (meth)acrylamide.

The examples also include styrene derivatives, such as aminostyrene and hydroxystyrene, and unsaturated carboxylic acids, such as (meth)acrylic acid, maleic anhydride, maleic acid, and fumaric acid.

Examples of the silicone component that can be incorporated into a silicone hydrogel blend include, but not limited to, a silicone-containing monomer, a silicone macromer, and a silicone prepolymer.

Examples of the silicone-containing monomer include a silicone-containing alkyl (meth)acrylate, a silicone-containing styrene derivative, and a silicone-containing fumaric acid diester.

Examples of the silicone-containing alkyl (meth)acrylate include trimethylsiloxydimethylsilylmethyl (meth)acrylate, trimethylsiloxydimethylsilylpropyl (meth)acrylate, methylbis(trimethylsiloxy)silylpropyl (meth)acrylate, and tris (trimethylsiloxy)silylpropyl (meth)acrylate, and amide derivatives thereof.

The examples also include mono[methylbis(trimethylsiloxy)siloxy]bis(trimethylsiloxy)silylpropyl (meth)acrylate, tris[methylbis(trimethylsiloxy)siloxy]silylpropyl (meth) acrylate, methylbis(trimethylsiloxy)silylpropylglyceryl (meth)acrylate, tris(trimethylsiloxy)silylpropylglyceryl (meth)acrylate, mono[methylbis(trimethylsiloxy)siloxy]bis (trimethylsiloxy)silylpropylglyceryl (meth)acrylate, trimethylsilylethyltetramethyldisiloxypropylglyceryl (meth) acrylate, trimethylsilylmethyl (meth)acrylate, trimethylsilylpropyl (meth)acrylate, trimethylsilylpropylglyceryl (meth)acrylate, trimethylsiloxydimethylsilylpropylglyceryl (meth)acrylate, methylbis(trimethylsiloxy)silylethyltetramethyldisiloxymethyl (meth)acrylate, tetramethyltriisopropylcyclotetrasiloxanylpropyl (meth)acrylate, tetramethyltriisopropylcyclotetrasiloxybis(trimethylsiloxy)silylpropyl (meth)acrylate, and (3-methacryloxy-2-hydroxypropyloxy)propylbis(trimethylsiloxy)methylsilane.

Examples of the silicone-containing styrene derivative include tris(trimethylsiloxy)silylstyrene, bis(trimethylsiloxy)methylsilylstyrene, (trimethylsiloxy)dimethylsilylstyrene, tris(trimethylsiloxy)siloxydimethylsilylstyrene, [bis(t-rimethylsiloxy)methylsiloxy]dimethylsilylstyrene, (trimethylsiloxy)dimethylsilylstyrene, heptamethyltrisiloxanylstyrene, nonamethyltetrasiloxanylstyrene, pentadecamethylheptasiloxanylstyrene, heneicosamethyldecasiloxanylstyrene, heptacosamethyltridecasiloxanylstyrene, hentriacontamethylpentadecasiloxanylstyrene, trimethylsiloxypentamethyldisiloxymethylsilylstyrene, tris(pentamethyldisiloxy)silylstyrene, tris(trimethylsiloxy)siloxybis(trimethylsiloxy)silylstyrene, bis(heptamethyltrisiloxy)methylsilylstyrene, tris[methylbis(trimethylsiloxy)siloxy]silylstyrene, trimethylsiloxybis[tris(trimethylsiloxy)siloxy]silylstyrene, heptakis(trimethylsiloxy)trisilylstyrene, nonamethyltetrasiloxyundecylmethylpentasiloxymethylsilylstyrene, tris[tris(trimethylsiloxy)siloxy]silylstyrene, (tristrimethylsiloxyhexamethyl)tetrasiloxy[tris(trimethylsiloxy)siloxy]trimethylsiloxysilylstyrene, nonakis(trimethylsiloxy)tetrasilylstyrene, bis(tridecamethylhexasiloxy)methylsilylstyrene, heptamethylcyclotetrasiloxanylstyrene, heptamethylcyclotetrasiloxybis(trimethylsiloxy)silylstyrene, tripropyltetramethylcyclotetrasiloxanylstyrene, and trimethylsilylstyrene.

Specific examples of the silicone-containing fumaric acid diester include bis(3-(trimethylsilyl)propyl) fumarate, bis(3-(pentamethyldisiloxanyl)propyl) fumarate, and bis(tris(trimethylsiloxy)silylpropyl) fumarate.

Examples of the silicone macromer include: monofunctional or difunctional polydimethylsiloxane; such polydimethylsiloxane methacrylated with a pendant hydrophilic group as described in U.S. Pat. No. 4,259,467; such a polydimethylsiloxane macromer having a polymerizable functional group as described in WO 97/00274 A1; and such a polysiloxane macromer having incorporated thereinto a hydrophilic monomer as described in WO 94/15980 A1.

In addition to the hydrophilic monomers and the silicone components listed above, a known monomer for a contact lens may also be used. For example, a cross-linking agent may be added to the photochromic curable composition for regulating its cross-linking density, softness, and hardness. An example of the cross-linking agent is a compound having a plurality of radical-polymerizable groups out of a (meth)acrylic group, a vinyl group, and an allyl group.

Examples of such cross-linking agent include allyl (meth)acrylate, vinyl (meth)acrylate, 4-vinylbenzyl (meth)acrylate, 3-vinylbenzyl (meth)acrylate, diethylene glycol mono (meth)acrylate, propylene glycol (meth)acrylate, (meth)acryloyloxyethyl (meth)acrylate, ethylene glycol di(meth)acrylate, diethylene glycol di(meth)acrylate, diethylene glycol diallyl ether, triethylene glycol di(meth)acrylate, tetraethylene glycol di(meth)acrylate, propylene glycol di(meth)acrylate, dipropylene glycol di (meth)acrylate, butanediol di(meth)acrylate, trimethylolpropane tri(meth)acrylate, 2,2-bis[p-(meth)acryloyloxyphenyl]hexafluoropropane, 2,2-bis[m-(meth)acryloyloxyphenyl]hexafluoropropane, 2,2-bis[o-(meth)acryloyloxyphenyl]hexafluoropropane, 2,2-bis[p-(meth)acryloyloxyphenyl]propane, 2,2-bis[m-(meth)acryloyloxyphenyl]propane, 2,2-bis[o-(meth)acryloyloxyphenyl]propane, 1,4-bis[2-(meth)acryloyloxyhexafluoroisopropyl]benzene, 1,3-bis[2-(meth)acryloyloxyhexafluoroisopropyl]benzene, 1,2-bis[2-(meth)acryloyloxyhexafluoroisopropyl]benzene, 1,4-bis[2-(meth)acryloyloxyisopropyl]benzene, 1,3-bis[2-(meth)acryloyloxyisopropyl]benzene, and 1,2-bis[2-(meth)acryloyloxyisopropyl]benzene. Those cross-linking agents may be used alone or in combination thereof.

In addition, a reinforcing monomer as well as the cross-linking agent may be added for regulating the hardness of a contact lens to impart desired softness thereto.

Examples of such reinforcing monomer include, as (meth)acrylic reinforcing monomers, linear, branched, or cyclic alkyl (meth)acrylates, such as methyl (meth)acrylate, ethyl (meth)acrylate, isopropyl (meth)acrylate, n-propyl (meth)acrylate, isobutyl (meth)acrylate, n-butyl (meth)acrylate, 2-ethylhexyl (meth)acrylate, n-octyl (meth)acrylate, n-decyl (meth)acrylate, n-dodecyl (meth)acrylate, t-butyl (meth)acrylate, pentyl (meth)acrylate, t-pentyl (meth)acrylate, hexyl (meth)acrylate, heptyl (meth)acrylate, nonyl (meth)acrylate, stearyl (meth)acrylate, cyclopentyl (meth)acrylate, and cyclohexyl (meth)acrylate.

The examples also include alkoxy derivatives of hydroxyalkyl (meth)acrylates, such as 2-methoxyethyl (meth)acrylate, 2-ethoxyethyl (meth)acrylate, 2-methoxyethoxyethyl (meth)acrylate, and 2-ethoxyethoxyethyl (meth)acrylate.

Examples of the reinforcing monomer include, as styrene-based reinforcing monomers,
styrene and alkylstyrenes, such as α-methylstyrene, methylstyrene, ethylstyrene, propylstyrene, butylstyrene, t-butylstyrene, isobutylstyrene, and pentylstyrene.

The examples also include alkyl-α-methylstyrenes, such as methyl-α-methylstyrene, ethyl-α-methylstyrene, propyl-α-methylstyrene, butyl-α-methylstyrene, t-butyl-α-methylstyrene, isobutyl-α-methylstyrene, and pentyl-α-methylstyrene.

Those reinforcing monomers may be used alone or in combination thereof.

Of the other polymerizable monomers each having the radical-polymerizable group listed above, when used in a contact lens application, the following suitable monomers are each preferably blended to provide a photochromic curable composition:

2-hydroxyethyl (meth)acrylate, N-vinylpyrrolidone, N-vinylpyrrolidinone, N-vinylglutarimide, N-vinyl-N-methylacetamide, N-vinylpyridine, methacrylic acid, glycerol methacrylate, N,N-diethylacrylamide, acryloylmorpholine, N,N-dimethylacrylamide, N-(2-hydroxyethyl) (meth)acrylamide, ethylene glycol di(meth)acrylate, tetraethylene glycol di(meth)acrylate, tris(trimethylsiloxy)silylstyrene, tris(trimethylsiloxy)silylpropyl (meth)acrylate and amide derivatives thereof, (3-methacryloxy-2-hydroxypropyloxy)propylbis(trimethylsiloxy)methylsilane, methylbis(trimethylsiloxy)silylpropyl (meth)acrylate, and diethylene glycol di(meth)acrylate.

In addition, when the chromene compound of the present invention is used in a contact lens application, the compound may be used in combination with a known blending agent in addition to the above-mentioned other polymerizable monomers. Examples thereof include a thickening agent and a refrigerant.

The thickening agent can improve compatibility between the respective monomers to reduce the amount of an unreacted component, and can regulate the viscosity of the photochromic curable composition. Further, when a person wears a contact lens containing the agent, the agent can give a moist feeling to the person's eye.

Although the thickening agent is not particularly limited, examples thereof include the following thickening agents:

various gums including polysaccharides, mucopolysaccharides, and heteropolysaccharides, such as chondroitin sulfate, hyaluronic acid, and gluconic acid, and salts thereof;

synthetic organic polymer compounds including polyvinyl alcohol, poly-N-vinylpyrrolidone, poly-N-vinylpiperidone, polyethylene glycol, polypropylene glycol, polyacrylamide, poly(meth)acrylic acid or salts thereof, a carboxy vinyl polymer, and a copolymer of poly-N-vinylpyrrolidone and dimethylaminoethyl methacrylate; and cellulose derivatives, such as hydroxyethyl cellulose, hydroxypropylmethyl cellulose, carboxy methyl cellulose, and methyl cellulose.

Examples thereof may also include starch derivatives.

The refrigerant can improve the compatibility between the respective monomers to reduce the amount of an unreacted component. In addition, when a person wears a contact lens containing the refrigerant, the refrigerant can give a refreshing feeling to the person's eye, and alleviate a foreign-body sensation and itchiness.

Examples of the refrigerant include anethole, eugenol, camphor, chlorobutanol, geraniol, cineole, borneol, menthol, limonene, *Dryobalanops aromatica* resin, fennel oil, cool mint oil, cinnamic oil, spearmint oil, mentha water, mentha oil, peppermint oil, bergamot oil, *Eucalyptus* oil, and rose oil.

Those refrigerants may be used alone or in combination thereof.

Such component (the blending agent) is preferably used in an amount in the range of from 0.001 part by mass to 5 parts by mass with respect to 100 parts by mass of the polymerizable monomers including the chromene compound of the present invention (total of the chromene compound of the present invention and the other polymerizable monomer).

In the present invention, the photochromic curable composition may be blended with an additive, such as a stabilizer, as required in addition to the chromene compound of the present invention or the photochromic composition, and the other polymerizable monomer. Such additive is described.

<Photochromic Curable Composition; Additive>

In the present invention, the durability of the photochromic curable composition can be further improved by blending the composition with an additive, such as a UV absorber, a light stabilizer, or an antioxidant, described below.

As the UV absorber, a known UV absorber, such as a benzophenone-based compound, a benzotriazole-based compound, a cyano acrylate-based compound, a triazine-based compound, or a benzoate-based compound, may be used. Of those, a cyano acrylate-based compound and a benzophenone-based compound are particularly preferred.

Such UV stabilizer is preferably used in an amount in the range of from 0.001 part by mass to 5 parts by mass with respect to 100 parts by mass of the polymerizable monomers including the chromene compound of the present invention (total of the chromene compound of the present invention and the other polymerizable monomer). In addition, a known hindered amine may be used as the light stabilizer, and a known hindered phenol may be used as the antioxidant. The light stabilizer and the antioxidant are each preferably used in an amount in the range of from 0.01 part by mass to 10 parts by mass with respect to 100 parts by mass of the polymerizable monomers including the chromene compound of the present invention.

<Method of using Photochromic Curable Composition; Optical Article>

In the present invention, examples of the other polymerizable monomer to be used in the photochromic curable composition are as described above, and the blending ratio of the other polymerizable monomer only needs to be appropriately determined in accordance with applications. However, the preferred blending amount of the chromene compound or the photochromic composition is as described above.

In the present invention, the photochromic curable composition can be prepared by mixing the chromene compound (photochromic composition) to be used, the other polymerizable monomer, and the additive or the like to be blended as required. An optical article having the chromene compound dispersed in a resin can be produced by: adding a polymerization catalyst and any other additive or the like as required to the resultant photochromic curable composition; and polymerizing the mixture with heat or light.

The chromene compound of the present invention may be utilized as a photochromic material in a wide variety of applications, and for example, may be utilized as various memory materials, such as: various memory materials that replace a silver halide photosensitive material; a copying material; a photosensitive member for printing; a memory material for a cathode-ray tube; a photosensitive material for a laser; and a photosensitive material for holography. In addition, the photochromic material using the chromene compound of the present invention may be utilized as a photochromic lens material, an optical filter material, a display material, an actinometer, or a material for decoration or the like.

For example, a known method may be adopted as a method of producing a photochromic lens using the chromene compound of the present invention as long as the method provides the lens showing uniform light-controlling performance. Specifically, there may be adopted a method including sandwiching a polymer film having uniformly dispersed therein the chromene compound of the present invention between lenses. Another example of the method is a method including: dispersing the chromene compound of the present invention in the other polymerizable monomer to provide a photochromic curable composition; and polymerizing the curable composition by a predetermined approach. Still another example thereof is a method including: dissolving the chromene compound of the present invention in, for example, a silicone oil; impregnating a lens surface with the solution at from 150° C. to 200° C. over from 10 minutes to 60 minutes; and further coating the surface with a curable substance to provide the photochromic lens. Further, for example, there is used a method including: applying the polymer film to the lens surface; and coating the surface with the curable substance to provide the photochromic lens.

In addition, the following may be performed: a coating agent formed of the photochromic curable composition is applied to the surface of a lens substrate, and the coating film is cured. At this time, the lens substrate may be subjected to surface treatment, such as surface treatment with an alkaline solution or plasma treatment, in advance. Further, a primer may be applied for improving adhesiveness between the substrate and the coating film together with such surface treatment or without performance of such surface treatment. Thus, an optical article coated with a polymer film having dispersed therein the chromene compound or the photochromic composition can be produced. In addition, it is also possible that a lens substrate is arranged in a cavity in advance, and the photochromic curable composition is poured thereinto and cured to produce an optical article of the shape corresponding to the cavity.

In addition, when the contact lens is produced, the following method is preferably adopted. A known contact lens production method may be adopted as long as the method provides the contact lens showing uniform light-controlling performance. For example, the following method (machining method) is given. The polymerization of the photochromic curable composition is performed in an appropriate vessel to provide a contact lens material formed of a photochromic cured body, the material being, for example, a rod shape, a block shape, or a plate shape. After that, the resultant contact lens material is subjected to machining, such as cutting or polishing, to be processed into a desired contact lens shape (photochromic optical article).

In addition, the following method (molding method) may be adopted. For example, the photochromic curable composition is polymerized in a forming die (casting mold) having a shape corresponding to the desired contact lens shape to provide a formed product (photochromic optical article) of a contact lens shape. Next, the formed product is subjected to finishing as required.

Further, the following method, that is, a method obtained by combining the machining method and the molding method may be adopted. The photochromic curable composition is polymerized in a forming die having a shape corresponding to at least one surface of the desired contact lens shape. Next, the other surface of the resultant photochromic cured body is subjected to machining to provide a contact lens (photochromic optical article).

In addition, a method, such as a spin casting method, may be adopted.

The resultant contact lens (photochromic optical article) may be subjected to, for example, low-temperature plasma treatment, atmospheric-pressure plasma treatment, or corona discharge treatment for the purpose of improving its surface characteristic. The low-temperature plasma treatment can provide a contact lens that is more excellent in wettability and/or contamination resistance. Probably because the chromene compound of the present invention has the specific ring Z group at its 13-position, and at least one of the phenyl groups at its 3-position has a specific radical-polymerizable group, when the compound is polymerized in combination with those hydrophilic monomers, the resultant photochromic cured body (optical article like a contact lens) exhibits an excellent effect. In particular, an optical article excellent in photochromic characteristic at from 33° C. to 38° C. and reduced in elution of the chromene compound itself can be obtained.

EXAMPLES

The present invention is described in more detail below by way of Examples, but the present invention is not limited to these Examples.

Example 1

1.0 Gram (2.8 mmol) of a naphthol compound represented by the following formula (19):

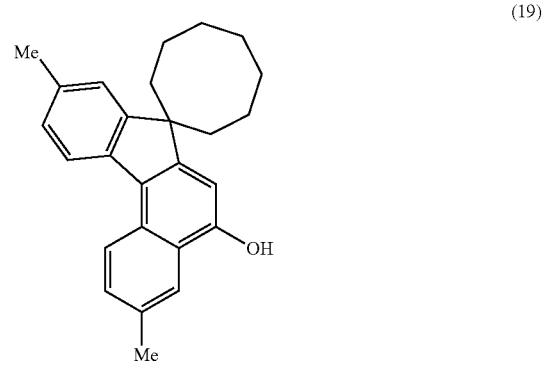 [SMILES: Cc1ccc2c(c1)C1(CCCCCCC1)c1cc(O)c3cc(C)ccc3c1-2]

and 12.0 g (3.4 mmol) of a 10 mass % solution of a propargyl alcohol compound having a reactive substituent (hydroxy group) represented by the following formula (20) in methyl ethyl ketone:

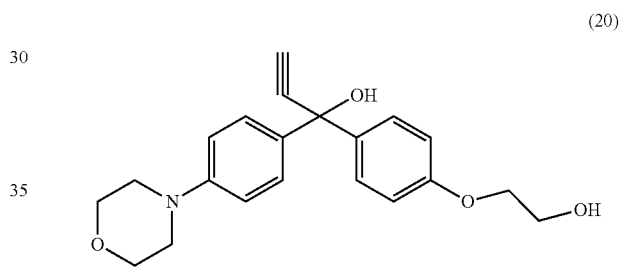

were dissolved in 50 mL of toluene. Further, 0.02 g of p-toluenesulfonic acid was added to the solution, and the mixture was stirred for 1 hour under heating reflux. After the reaction, the solvent was removed, and the residue was purified by chromatography on silica gel to provide 1.4 g of a white powdery product (precursor). The yield was 72%.

The resultant precursor was dissolved in 0.7 g (6.9 mmol) of triethylamine and 30 mL of dichloromethane, and the solution was cooled with ice. 0.3 Gram (2.9 mmol) of acryloyl chloride was slowly dropped into the solution. After the reaction, the solvent was removed, and the residue was purified by chromatography on silica gel to provide 1.3 g of a white powdery product (chromene compound). The yield was 86%. The elemental analysis values of the product were as follows: C: 80.48%, H: 6.91%, N: 1.86%. The values coincided extremely well with the following calculated values of $C_{49}H_{49}NO_6$: C: 80.51%, H: 6.89%, N: 1.88%.

In addition, the proton nuclear magnetic resonance spectrum of the product was measured. As a result, the compound showed 20H peaks based on the methylene proton of a cyclooctane ring and the methyl proton of a methyl group at a δ of from about 1.0 ppm to about 3.0 ppm, 12H peaks based on an ethyleneoxy group and a morpholino group at a δ of from about 3.0 ppm to about 5.0 ppm, and 19H peaks based on an aromatic proton and the proton of an alkene at a δ of from about 5.6 ppm to about 9.0 ppm.

Further, the $^{13}C$ nuclear magnetic resonance spectrum of the product was measured. As a result, the compound showed a peak based on the carbon atoms of an aromatic ring and an acrylic group at a δ of from about 110 ppm to about 220 ppm, a peak based on the carbon atoms of an alkene at a δ of from about 80 ppm to about 140 ppm, and a peak based on the carbon atoms of an alkyl group at a δ of from about 20 ppm to about 75 ppm.

It was recognized from the foregoing results that the isolated product was a compound represented by the following formula (21).

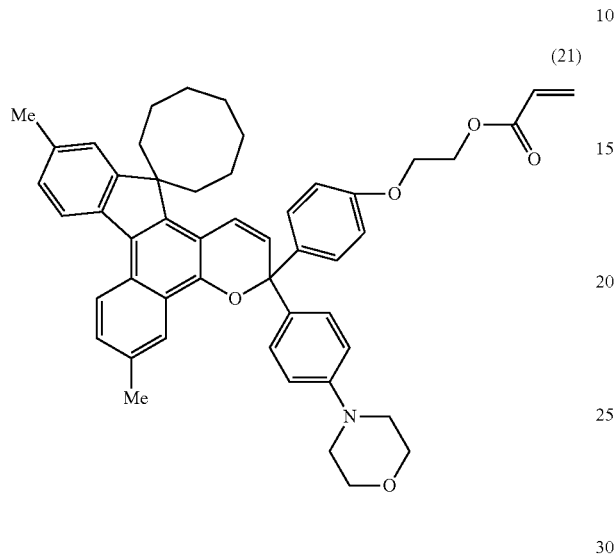

(21)

Examples 2 to 10

Such chromene precursors and chromene compounds as shown in Tables 4 to 6 were synthesized by using naphthol compounds and propargyl alcohol compounds each having a reactive substituent shown in Tables 1 to 3 in the same manner as in Example 1. The structural analysis of each of the resultant products was performed by using the same structure identification methods as those of Example 1. As a result, it was recognized that the products were compounds represented by structural formulae shown in Tables 4 to 6. In addition, the elemental analysis values of those compounds, calculated values determined from the structural formulae of the respective compounds, and the characteristic peaks of the $^1$H-NMR spectra thereof are shown in Table 7.

TABLE 1

| Example | Naphthol compound | Propargyl alcohol compound |
|---|---|---|
| 2 | | |

TABLE 1-continued
| Example | Naphthol compound | Propargyl alcohol compound |
|---|---|---|
| 3 | 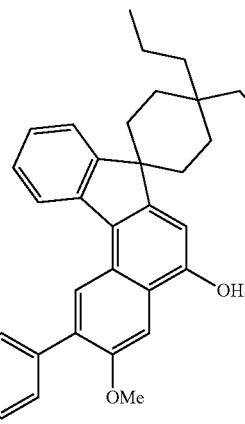 | 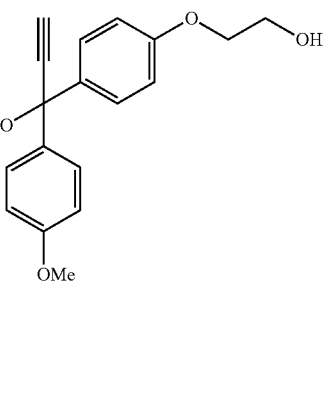 |
| 4 | 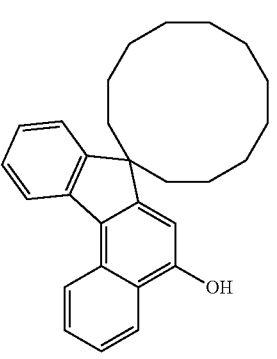 [SMILES: Oc1cc2c(c3ccccc13)-c1ccccc1C21CCCCCCCCCCC1] | 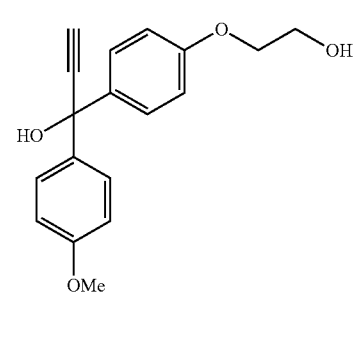 [SMILES: C#CC(O)(c1ccc(OC)cc1)c1ccc(OCCO)cc1] |
| 5 | 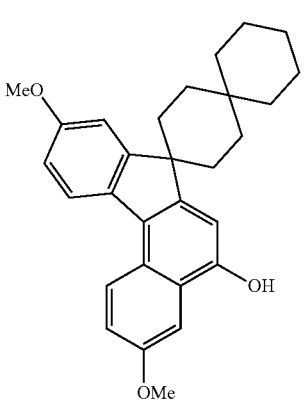 [SMILES: COc1ccc2c(c1)C1(CCC3(CCCCC3)CC1)c1cc(O)c3cc(OC)ccc3c1-2] | 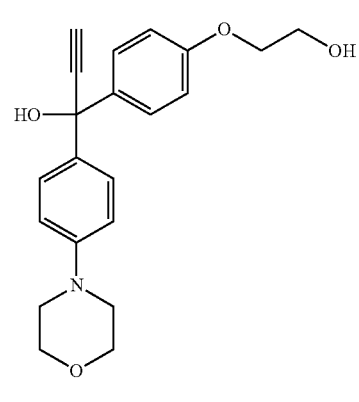 [SMILES: C#CC(O)(c1ccc(OCCO)cc1)c1ccc(N2CCOCC2)cc1] |

TABLE 2

| Example | Naphthol compound | Propargyl alcohol compound |
| --- | --- | --- |
| 6 | | |
| 7 | | |
| 8 | | |
| 9 | | |

TABLE 3
| Example | Naphthol compound | Propargyl alcohol compound |
|---|---|---|
| 10 | 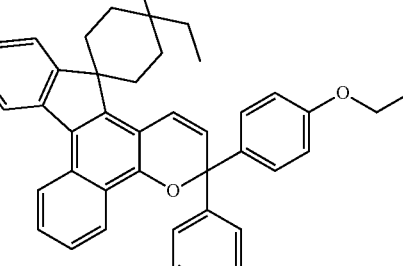 | 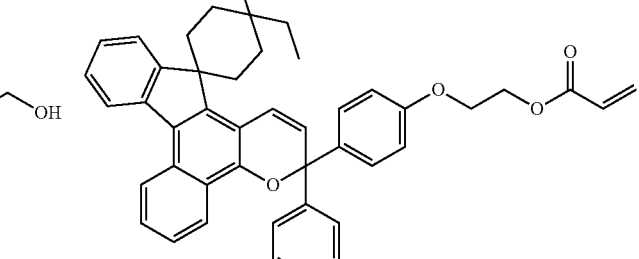 |
TABLE 4
| Example | Precursor | Product |
|---|---|---|
| 2 | 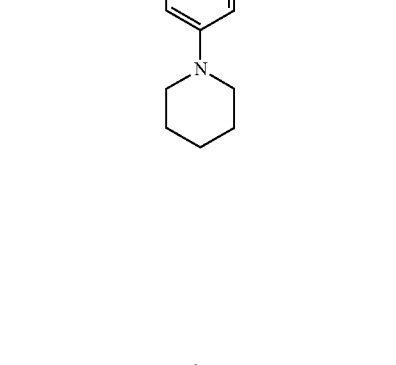 | |
| 3 | 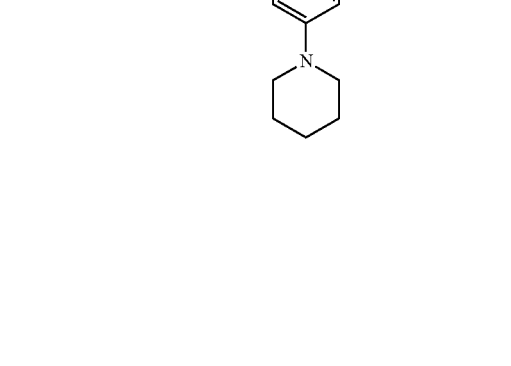 | |

TABLE 4-continued

| Example | Precursor | Product |
|---|---|---|
| 4 | (structure) | (structure) |
| 5 | (structure) | (structure) |

TABLE 5

| Example | Precursor | Product |
|---|---|---|
| 6 | (structure) | (structure) |

TABLE 5-continued
| Example | Precursor | Product |
|---|---|---|
| 7 | 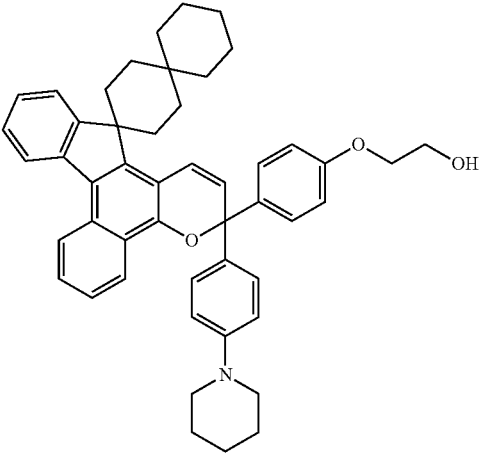 [SMILES: OCCOc1ccc(C2(c3ccc(N4CCCCC4)cc3)C=Cc3c4c(c5ccccc5c3O2)-c2ccccc2C42CCC3(CCCCC3)CC2)cc1] | 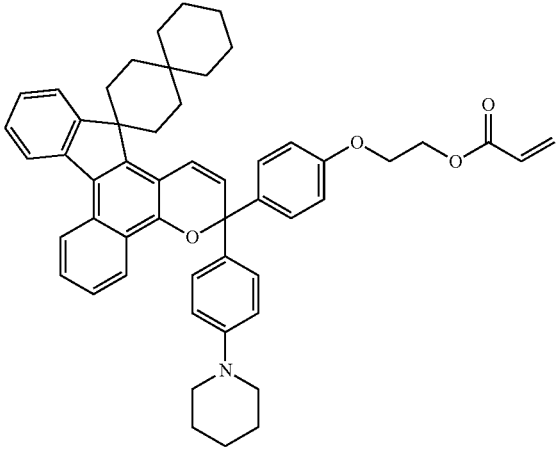 [SMILES: C=CC(=O)OCCOc1ccc(C2(c3ccc(N4CCCCC4)cc3)C=Cc3c4c(c5ccccc5c3O2)-c2ccccc2C42CCC3(CCCCC3)CC2)cc1] |
| 8 | 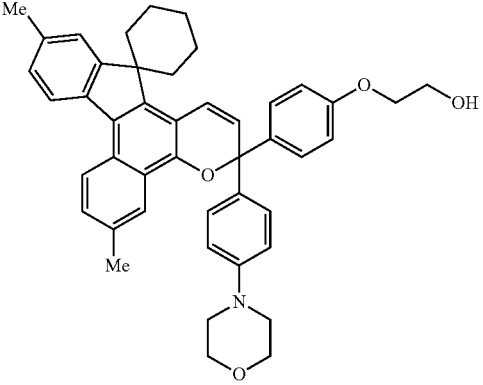 [SMILES: Cc1ccc2c(c1)C1(CCCCC1)c1c3c(c4cc(C)ccc4c1-2)OC(c1ccc(OCCO)cc1)(c1ccc(N2CCOCC2)cc1)C=C3] | 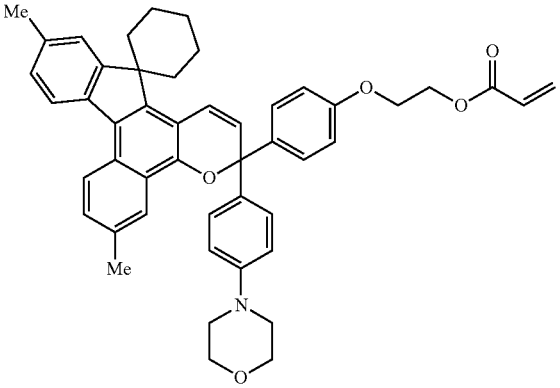 [SMILES: C=CC(=O)OCCOc1ccc(C2(c3ccc(N4CCOCC4)cc3)C=Cc3c4c(c5ccc(C)cc5c3O2)-c2ccc(C)cc2C42CCCCC2)cc1] |
| 9 | 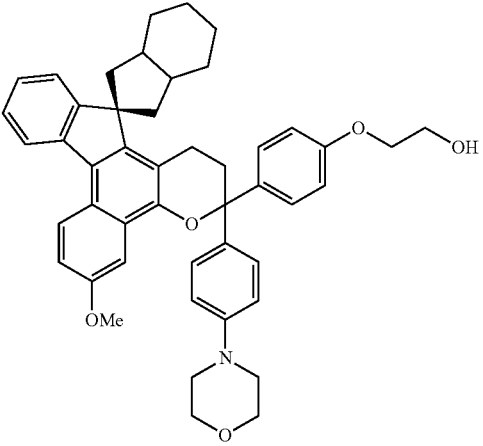 | 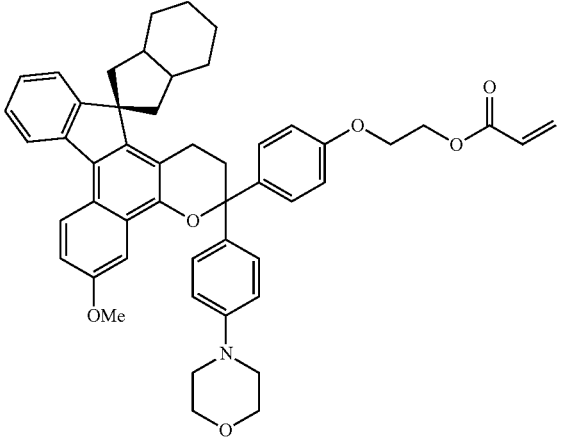 |

TABLE 6

| Example | Precursor | Product |
|---------|-----------|---------|
| 10 | (structure) | (structure) |

TABLE 7

| Example | Compound No. | Calculated value | | | | Measured value | | | | 1H-NMR |
|---------|--------------|------|------|------|------|------|------|------|------|--------|
| | | C | H | N | S | C | H | N | S | |
| 2 | 2 | 82.33 | 7.18 | 1.88 | — | 82.35 | 7.16 | 1.87 | — | δ0-5.0 ppm 32 H<br>δ5.0-9.0 ppm 21 H |
| 3 | 3 | 80.07 | 6.84 | — | — | 80.02 | 6.89 | — | — | δ0-5.0 ppm 35 H<br>δ5.0-9.0 ppm 23 H |
| 4 | 4 | 81.86 | 7.01 | — | — | 81.89 | 7.00 | — | — | δ0-5.0 ppm 29 H<br>δ5.0-9.0 ppm 21 H |
| 5 | 5 | 77.82 | 6.78 | 1.71 | — | 77.84 | 6.79 | 1.72 | — | δ0-5.0 ppm 36 H<br>δ5.0-9.0 ppm 19 H |
| 6 | 6 | 81.86 | 7.01 | — | — | 81.88 | 7.00 | — | — | δ0-5.0 ppm 31 H<br>δ5.0-9.0 ppm 19 H |
| 7 | 7 | 82.62 | 7.07 | 1.85 | — | 82.60 | 7.08 | 1.83 | — | δ0-5.0 ppm 32 H<br>δ5.0-9.0 ppm 21 H |
| 8 | 8 | 75.32 | 6.90 | 3.19 | — | 75.33 | 6.89 | 3.20 | — | δ0-5.0 ppm 41 H<br>δ5.0-9.0 ppm 19 H |
| 9 | 9 | 79.03 | 6.50 | 1.84 | — | 79.00 | 6.48 | 1.88 | — | δ0-5.0 ppm 29 H<br>δ5.0-9.0 ppm 20 H |
| 10 | 10 | 77.09 | 6.47 | — | 4.12 | 77.05 | 6.45 | — | 4.15 | δ0-5.0 ppm 31 H<br>δ5.0-9.0 ppm 19 H |

Examples 11 to 22

Physical Property Evaluations of Produced Photochromic Contact Lenses Photochromic Optical Articles A product obtained by blending tris(trimethylsiloxy)silylpropyl methacrylate, dimethyl acrylamide, 2-hydroxyethyl methacrylate, and ethylene glycol dimethacrylate serving as radical-polymerizable monomers at blending ratios of 60 parts by mass, 30 parts by mass, 8 parts by mass, and 2 parts by mass, respectively was used as a photochromic curable composition. 1 Part by mass of each of the chromene compounds Nos. 1 to 10 obtained in Examples 1 to 10 was added to 100 parts by mass of the mixture of the radical-polymerizable monomers, and the materials were sufficiently mixed. After that, 0.3 part by mass of V65 (2,2'-azobis(2,4-dimethylvaleronitrile)) that was a thermal polymerization initiator was added to the mixture, and the materials were sufficiently mixed to provide a photochromic curable composition. The resultant photochromic curable composition was poured into a casting mold including a glass plate and a polyethylene terephthalate (PTEF) sheet having a thickness of 0.1 mm, and was subjected to cast polymerization. In the polymerization, the composition was held at 90° C. for 1 hour through the use of an air furnace. After the completion of the polymerization, the polymer was removed from the glass plate of the casting mold. The resultant photochromic cured body (thickness: 0.1 mm) was immersed in distilled water at 40° C. for 3 hours or more to provide a photochromic contact lens (photochromic optical article).

The resultant photochromic contact lens was subjected to the following evaluations. The results are shown in Table 8.
(1) Photochromic Characteristics
[1] Local maximum absorption wavelength (λmax): The local maximum absorption wavelength of the lens was the local maximum absorption wavelength thereof after its color development determined with a spectrophotometer manufactured by Otsuka Electronics Co., Ltd. (instant multichannel photodetector MCPD3000), and was used as an indicator of the color tone thereof at the time of the color development.

[2] Color development density at 36° C. ($A_{36}$): The color development density of the lens at 36° C. was a difference between the absorbance {ε(180)} thereof after light irradiation at 36° C. for 180 seconds and the absorbance {ε(0)} thereof at the time of no light irradiation at the local maximum absorption wavelength, and was used as an indicator of the color development density thereof. It can be said that as the value becomes higher, the photochromic property of the lens becomes more excellent.

[3] Color fading half-life at 36° C. [$\tau_{1/2}$ (sec.)] The color fading half-life of the lens at 36° C. was a time period required for the absorbance of the sample at the local maximum absorption wavelength to reduce to one half of {ε(180)-ε(0)} when light irradiation was performed at 36° C. for 180 seconds, and then the light irradiation was stopped, and the color fading half-life was used as an indicator of the color fading rate thereof. As the time period becomes shorter, the color fading rate becomes faster.

[4] Residual ratio ($A_{50}/A_0 \times 100$): The resultant photochromic cured body was subjected to accelerated deterioration with a xenon weather meter X25 manufactured by Suga Test Instruments Co., Ltd. for 50 hours. The color development density evaluations were performed before and after the test, and the color development density ($A_0$) of the cured body before the test and the color development density ($A_{50}$) thereof after the test were measured. A ratio ($A_{50}/A_0$) between the densities was defined as a residual ratio, and was used as an indicator of the durability of the color development of the cured body. As the residual ratio becomes higher, the durability of the color development becomes higher.

(2) Determination of Amount of Eluted Component 5.0 Grams of the resultant photochromic cured body (optical article) was subjected to Soxhlet extraction with methanol for 48 hours, and the residual component was extracted. The extract was analyzed by high performance liquid chromatography (HPLC), and the elution ratio of the eluted chromene compound was calculated. The amount of the eluate was determined by an internal standard method including using phenanthrene as a standard sample.

Elution ratio: (determined value of amount of eluate)/(weight of photochromic cured body× 0.01)×100

The denominator "weight of photochromic cured body× 0.01" represents the amount of the chromene compound used at the time of the production of the cured body.

TABLE 8

| Example | Compound No | $\lambda_{max}$ (nm) | $A_{36}$ (—) | $\tau_{1/2}$ (sec) | $A_{50}/A_0 \times$ 100 (%) | Elution ratio (%) |
|---|---|---|---|---|---|---|
| 11 | 1 | 455 | 0.32 | 20 | 76 | 0.6 |
|  |  | 585 | 0.60 | 20 | 76 |  |
| 12 | 2 | 455 | 0.19 | 7 | 72 | 0.9 |
|  |  | 582 | 0.52 | 7 | 72 |  |
| 13 | 3 | 440 | 0.34 | 10 | 76 | 0.8 |
|  |  | 560 | 0.34 | 10 | 76 |  |
| 14 | 4 | 426 | 0.40 | 31 | 75 | 0.9 |
|  |  | 542 | 0.76 | 30 | 74 |  |
| 15 | 5 | 453 | 0.40 | 25 | 75 | 0.5 |
|  |  | 595 | 0.77 | 26 | 75 |  |
| 16 | 6 | 429 | 0.26 | 11 | 74 | 0.7 |
|  |  | 550 | 0.50 | 10 | 74 |  |
| 17 | 7 | 455 | 0.20 | 9 | 73 | 0.9 |
|  |  | 587 | 0.52 | 9 | 74 |  |
| 20 | 8 | 456 | 1.08 | 70 | 70 | 0.8 |
|  |  | 556 | 0.47 | 70 | 71 |  |
| 21 | 9 | 457 | 0.30 | 13 | 76 | 0.5 |
|  |  | 586 | 0.56 | 13 | 76 |  |
| 22 | 10 | 454 | 0.65 | 28 | 72 | 0.8 |
|  |  | 564 | 0.45 | 28 | 73 |  |

Comparative Examples 1 to 3

For comparison, photochromic contact lenses (photochromic optical articles) were obtained by using compounds represented by the following formulae (A) to (C) in the same manner as in Example 11, and their characteristics were evaluated. The results are shown in Table 9.

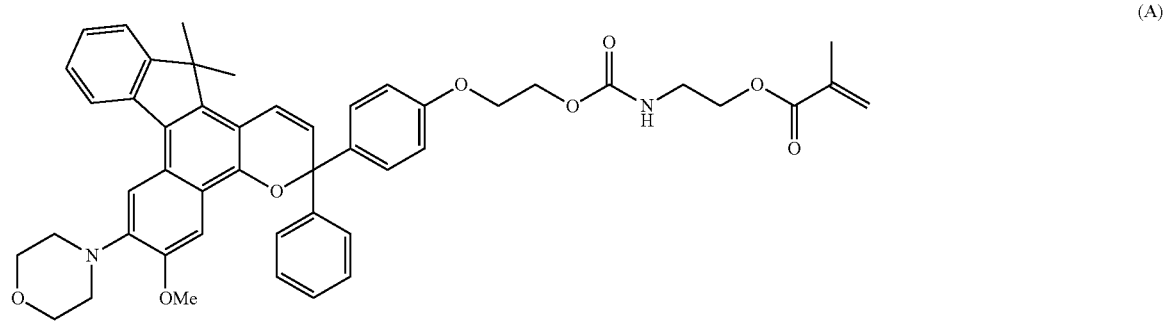

(A)

(B)

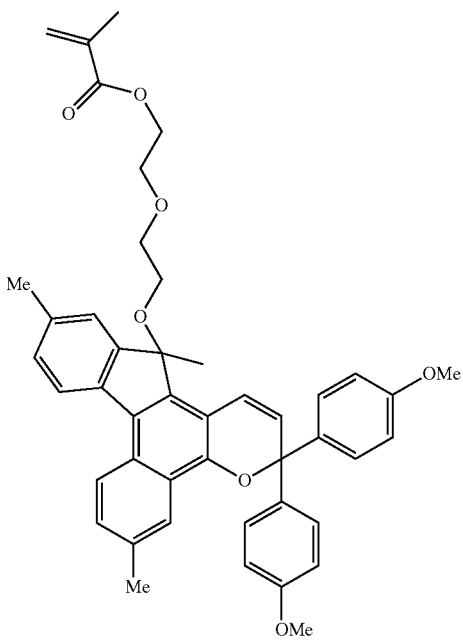

-continued (C)

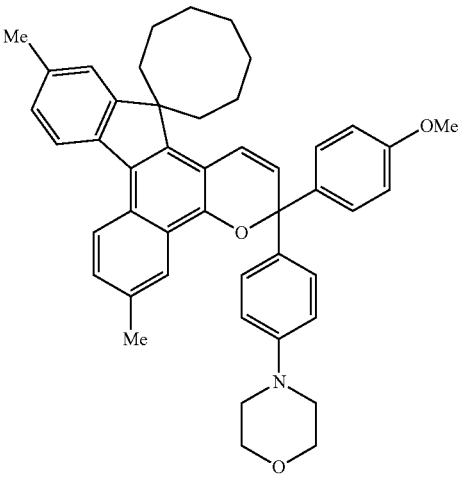

TABLE 9

| Comparative Example | Compound No | $\lambda_{max}$ (nm) | $A_{36}$ (-) | $\tau_{1/2}$ (sec) | $A_{50}/A_0 \times 100$ (%) | Elution ratio (%) |
|---|---|---|---|---|---|---|
| 1 | (A) | 456 | 1.20 | 108 | 75 | 1.0 |
|   |     | 555 | 0.52 | 108 | 74 |     |
| 2 | (B) | 436 | 0.16 | 9 | 35 | 0.9 |
|   |     | 557 | 0.30 | 9 | 36 |     |
| 3 | (C) | 453 | 0.32 | 19 | 77 | 86.0 |
|   |     | 586 | 0.58 | 19 | 77 |     |

As shown in Table 8 and Table 9, the photochromic contact lens (photochromic optical article) obtained by curing the photochromic curable composition of the present invention is suppressed from causing the elution of the photochromic compound, and has high durability. In addition, the lens was excellent in photochromic characteristics at around body temperature.

Examples 23 and 24

Production and Evaluation of Photochromic Laminates Photochromic Cured Bodies

A product obtained by blending polyethylene glycol dimethacrylate (average molecular weight: 736), polyethylene glycol dimethacrylate (average molecular weight: 536), trimethylolpropane trimethacrylate, γ-methacryloyloxypropyltrimethoxysilane, and glycidyl methacrylate serving as radical-polymerizable monomers at blending ratios of 45 parts by mass, 7 parts by mass, 40 parts by mass, 2 parts by mass, and 1 part by mass, respectively was used as a photochromic curable composition. 1 Part by mass of the chromene compound (the compound No. 4 or the compound No. 5) obtained in Example 4 or 5 was added to 100 parts by mass of the mixture of the radical-polymerizable monomers, and the materials were sufficiently mixed. After that, 0.3 part by mass of phenylbis(2,4,6-trimethylbenzoyl)phosphine oxide (product name: Irgacure 819, manufactured by BASF SE), 3 parts by mass of bis(1,2,2,6,6-pentamethyl-4-piperidyl) sebacate (molecular weight: 508), 3 parts by mass of ethylenebis(oxyethylene) bis[3-(5-tert-butyl-4-hydroxy-m-tolyl)propionate] (manufactured by Ciba Specialty Chemicals, Irganox 245), and 0.1 part by mass of a product available under the product name "L7001" from Dow Corning Toray Co., Ltd. were added to the mixture, and the materials were sufficiently mixed to provide a photochromic curable composition.

A photochromic laminate was obtained through use of the curable composition by a lamination method. A polymerization method is described below.

First, a thiourethane-based plastic lens having a center thickness of 2 mm and a refractive index of 1.60 was prepared as an optical substrate. The thiourethane-based plastic lens was subjected to alkaline etching with a 10% aqueous solution of sodium hydroxide at 50° C. for 5 minutes in advance, and was then sufficiently washed with distilled water.

The surface of the plastic lens was coated with a moisture-curable primer (product name: TR-SC-P, manufactured by Tokuyama Corporation) with a spin coater (1H-DX2, manufactured by Mikasa Co., Ltd.) at a number of revolutions of 70 rpm for 15 seconds and then at 1,000 rpm for 10 seconds. After that, the lens was spin-coated with about 2 g of the photochromic composition obtained in the foregoing at a number of revolutions of 60 rpm over 40 seconds and then at 600 rpm over from 10 seconds to 20 seconds so that the thickness of a photochromic coating layer became 40 μm.

The lens having applied to its surface the coating agent as described above was irradiated with light from a metal halide lamp having an output of 200 mW/cm² for 90 seconds in a nitrogen gas atmosphere so that the coating film was cured. After that, the resultant was further heated at 110° C. for 1 hour to produce a photochromic laminate including a photochromic layer.

The characteristics of the resultant photochromic laminate including the photochromic layer were evaluated in the same manner as in Example 11. The results are shown in Table 10.

TABLE 10

| Example | Compound No | $\lambda_{max}$ (nm) | $A_{36}$ (-) | $\tau_{1/2}$ (sec) | $A_{50}/A_0 \times 100$ (%) | Elution ratio (%) |
|---|---|---|---|---|---|---|
| 23 | 4 | 433 | 0.27 | 28 | 80 | 1.2 |
|  |  | 553 | 0.55 | 28 | 81 |  |
| 24 | 5 | 465 | 0.28 | 24 | 83 | 1.5 |
|  |  | 605 | 0.57 | 24 | 84 |  |

Example 25

First Step 9.8 Grams (42 mmol) of 4-chloro-4'-hydroxybenzophenone, 9.9 g (71.6 mmol) of potassium carbonate, and 100 mL of N,N-dimethylformamide were added, and were heated at 80° C. A solution of 19.6 g (50 mmol) of pentaethylene glycol monotosylate in 100 mL of N,N-dimethylformamide was slowly dropped into the mixture, and the whole was heated at 80° C. After the completion of the reaction, the resultant was cooled with ice, and 500 mL of toluene, 500 mL of tetrahydrofuran, and 500 mL of water were added to perform liquid separation. Water washing was repeated until the resultant became nearly neutral, followed by the concentration of the solvent. After that, the concentrate was purified by silica gel column chromatography to provide a compound represented by the following formula (22) in 85% yield.

(22)

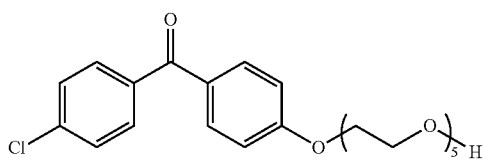

Second Step 16.2 Grams (36 mmol) of the compound represented by the formula (22), 100 mL of N,N-dimethylformamide, and 5.4 g (79 mmol) of imidazole were added and stirred, and then the mixture was cooled with ice water. A solution of 5.9 g (39 mmol) of tert-butyldimethylchlorosilane in 60 mL of N,N-dimethylformamide was slowly dropped into the mixture.

After the completion of the reaction, 500 mL of toluene and 160 mL of water were added to perform liquid separation, followed by the concentration of the solvent. After the concentration of the solvent, the concentrate was purified by silica gel column chromatography to provide a compound represented by the following formula (23) in 98% yield.

(23)

Third Step 19.8 Grams (35 mmol) of the compound represented by the formula (23), 4.3 g (49 mmol) of morpholine, 4.0 g (42 mmol) of sodium tert-butoxide, and 200 mL of toluene were added, and were stirred under reduced pressure to remove dissolved oxygen. After that, 0.33 g (0.7 mmol) of 2-dicyclohexylphosphino-2',4',6'-triisopropylbiphenyl and 0.16 g (0.2 mmol) of tris (dibenzylideneacetone) dipalladium were added to the residue, and the mixture was heated to 80° C. After the completion of the reaction, the mixture was cooled to room temperature, and insoluble matter was filtered out. The filtrate was washed well with 100 mL of toluene, and then 300 mL of water was added to the filtrate to perform liquid separation. The liquid separation was repeated until the pH of the filtrate became from 7 to 8, followed by the evaporation of the solvent. The residue was purified by silica gel column chromatography to provide a compound represented by the following formula (24) in 89% yield.

(24)

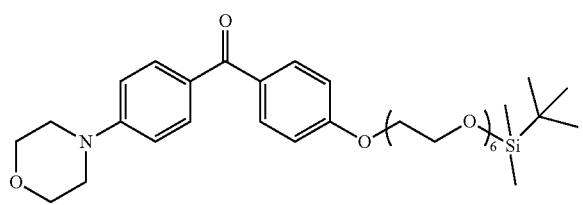

Fourth Step 19.2 Grams (31 mmol) of the compound represented by the formula (24) and 400 mL of N,N-dimethylformamide were added and stirred, and then the mixture was cooled to from 5° C. to 10° C. 4.3 Grams (47 mmol) of the ethylenediamine complex of lithium acetylide was slowly added to the mixture.

The mixture was subjected to a reaction at from 5° C. to 10° C. for 7 hours, and then 600 mL of toluene and 400 mL of water were added to perform liquid separation. The liquid separation was repeated until the pH of the resultant became from 7 to 8, followed by the concentration of the solvent. Thus, a compound represented by the following formula (25) was obtained.

(25)

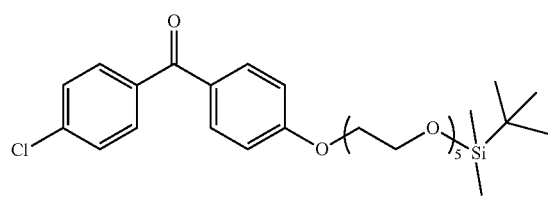

Fifth Step 4.6 Grams (10 mmol) of a compound represented by the following formula (26):

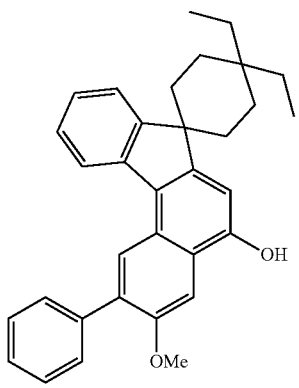

(26)

7.7 g (12 mmol) of the compound represented by the formula (25), 0.2 g (1 mmol) of pyridinium p-toluenesulfonate, and 100 mL of toluene were added, and were subjected to a reaction at 90° C. After the reaction, 100 mL of water was added to perform liquid separation. The liquid separation was repeated until the pH of the resultant became from 6 to 7. The solvent was concentrated, and 100 mL of tetrahydrofuran was added to the residue. The mixture was cooled to from 0° C. to 5° C., and then 11 mL of a 1 mol/L solution of tetrabutylammonium fluoride in tetrahydrofuran was slowly dropped into the mixture. The mixture was stirred at from 0° C. to 5° C. until its reaction was completed. After that, 30 mL of water and 30 mL of toluene were added to perform liquid separation. The liquid separation was repeated until the pH of the resultant became from 6 to 7, followed by the concentration of the solvent. The concentrate was purified by silica gel column chromatography to provide a precursor represented by the following formula (27) in 85% yield.

(27)

Sixth Step

A chromene compound represented by the following formula (28) was obtained in 88% yield by using the precursor represented by the formula (27) in the same manner as in Example 1 except that methacryloyl chloride was used instead of acryloyl chloride.

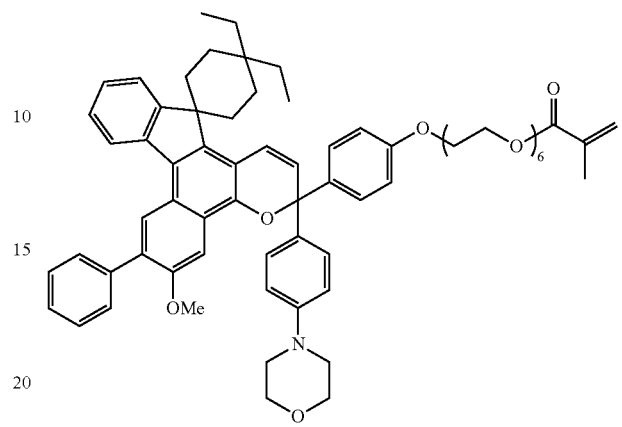

(28)

The elemental analysis values of the product were as follows: C: 76.00%, H: 7.28%, N: 1.37%. The values coincided extremely well with the following calculated values of $C_{66}H_{75}NO_{10}$: C: 76.05%, H: 7.25%, N: 1.34%.

In addition, the proton nuclear magnetic resonance spectrum of the product was measured. As a result, the compound showed 21H peaks based on the methylene proton of a cyclohexane ring, a methyl group, and an ethyl group at a δ of from about 1.0 ppm to about 3.0 ppm, 31H peaks based on a methoxy group, an ethyleneoxy group, and a morpholino group at a δ of from about 3.0 ppm to about 5.0 ppm, and 23H peaks based on an aromatic proton and the proton of an alkene at a δ of from about 5.6 ppm to about 9.0 ppm.

Further, the $^{13}C$ nuclear magnetic resonance spectrum of the product was measured. As a result, the compound showed a peak based on the carbon atoms of an aromatic ring and a carbonyl group at a δ of from about 110 ppm to about 220 ppm, a peak based on the carbon atoms of an alkene at a δ of from about 80 ppm to about 140 ppm, and a peak based on the carbon atoms of an alkyl group at a δ of from about 20 ppm to about 75 ppm.

Example 26

First Step

A propargyl alcohol compound represented by the following formula (29) was synthesized in the same manner as in Example 25 except that: 4-hydroxy-4'-propoxybenzophenone was used instead of 4-chloro-4'-hydroxybenzophenone; and propylene glycol monotosylate was used instead of pentaethylene glycol monotosylate.

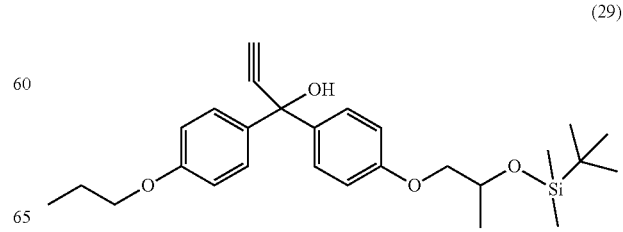

(29)

Second Step

A chromene compound represented by the following formula (31) was obtained in the same manner as in Example 25 except that: a compound represented by the following formula (30):

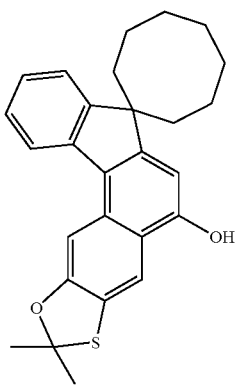

(30)

was used instead of the naphthol compound represented by the formula (26); and the compound represented by the formula (29) was used instead of the compound represented by the formula (25).

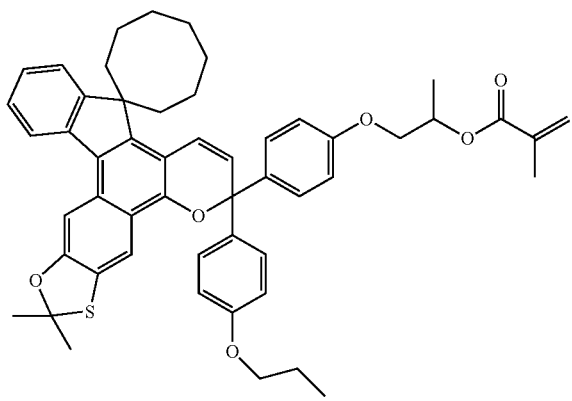

(31)

The elemental analysis values of the product were as follows: C: 77.41%, H: 7.24%, S: 3.96%. The values coincided extremely well with the following calculated values of $C_{52}H_{54}O_6S$: C: 77.39%, H: 6.74% S: 3.97%.

In addition, the proton nuclear magnetic resonance spectrum of the product was measured. As a result, the compound showed 31H peaks based on the methylene proton of a cyclooctane ring, a methyl group, and a propyl group at a δ of from about 1.0 ppm to about 3.0 ppm, 5H peaks based on a methoxy group, an ethyleneoxy group, and a propoxy group at a δ of from about 3.0 ppm to about 5.0 ppm, and 18H peaks based on an aromatic proton and the proton of an alkene at a δ of from about 5.6 ppm to about 9.0 ppm.

Further, the $^{13}C$ nuclear magnetic resonance spectrum of the product was measured. As a result, the compound showed a peak based on the carbon atoms of an aromatic ring and a carbonyl group at a δ of from about 110 ppm to about 220 ppm, a peak based on the carbon atoms of an alkene at a δ of from about 80 ppm to about 140 ppm, and a peak based on the carbon atoms of an alkyl group at a δ of from about 20 ppm to about 75 ppm.

Example 27

First Step

A compound represented by the following formula (32) was obtained in 95% yield in the same manner as in Example 25 except that 4-(2-hydroxy) ethoxy-4-methylbenzophenone was used instead of the compound represented by the formula (22).

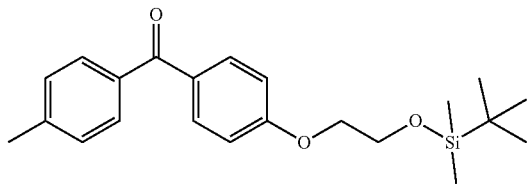

(32)

Second Step

A chromene compound represented by the following formula (34) was obtained by performing the reaction in the same manner as in Example 25 except that: the compound represented by the formula (32) was used instead of the compound represented by the formula (23); and a compound represented by the formula (33):

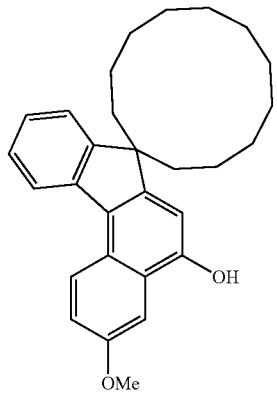

(33)

was used instead of the compound represented by the formula (26).

(34)

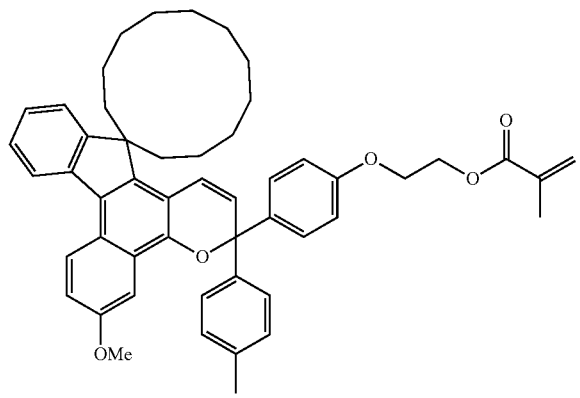

The elemental analysis values of the product were as follows: C: 82.03%, H: 7.25%. The values coincided extremely well with the following calculated values of $C_{51}H_{54}O_5$: C: 82.00%, H: 7.29%.

In addition, the proton nuclear magnetic resonance spectrum of the product was measured. As a result, the compound showed 28H peaks based on the methylene proton of a cyclododecane ring and a methyl group at a δ of from about 1.0 ppm to about 3.0 ppm, 7H peaks based on a methoxy group and an ethyleneoxy group at a δ of from about 3.0 ppm to about 5.0 ppm, and 19H peaks based on an aromatic proton and the proton of an alkene at a δ of from about 5.6 ppm to about 9.0 ppm.

Further, the $^{13}C$ nuclear magnetic resonance spectrum of the product was measured. As a result, the compound showed a peak based on the carbon atoms of an aromatic ring and a carbonyl group at a δ of from about 110 ppm to about 220 ppm, a peak based on the carbon atoms of an alkene at a δ of from about 80 ppm to about 140 ppm, and a peak based on the carbon atoms of an alkyl group at a δ of from about 20 ppm to about 75 ppm.

Examples 28 to 37

Such chromene precursors and chromene compounds as shown in Tables 13 and 14 were synthesized by using naphthol compounds and propargyl alcohol compounds shown in Tables 11 and 12 in the same manner as in Example 1. The structural analysis of each of the resultant products was performed by using the same structure identification methods as those of Example 1. As a result, it was recognized that the products were compounds represented by structural formulae shown in Tables 13 and 14. In addition, the elemental analysis values of those compounds, calculated values determined from the structural formulae of the respective compounds, and the characteristic peaks of the $^1H$-NMR spectra thereof are shown in Table 15.

TABLE 11

| Example | Naphthol compound | Propargyl alcohol compound |
|---|---|---|
| 28 | | |
| 29 | | |

TABLE 11-continued
| Example | Naphthol compound | Propargyl alcohol compound |
|---|---|---|
| 30 | 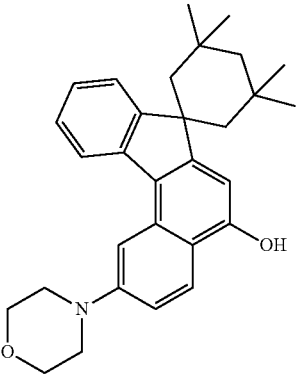 [SMILES: CC1(C)CC(C)(C)CC2(C1)c1ccccc1-c1c2cc(O)c2ccc(N3CCOCC3)cc12] | 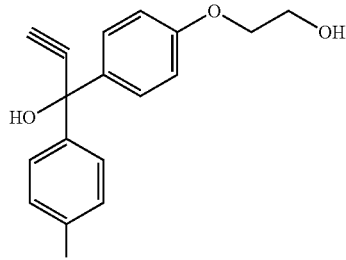 |
| 31 | 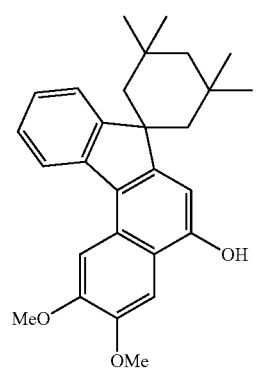 | 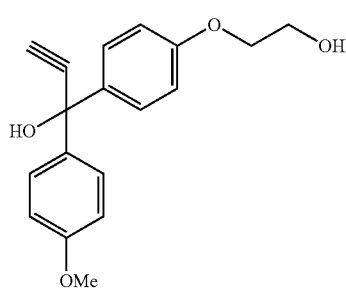 [SMILES: C#CC(O)(c1ccc(OC)cc1)c1ccc(OCCO)cc1] |
| 32 | 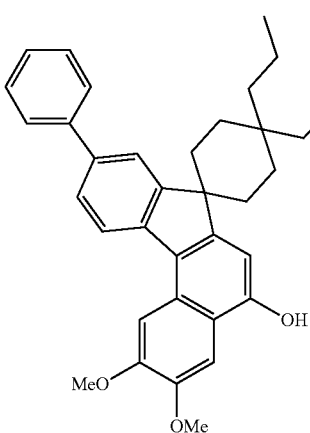 | 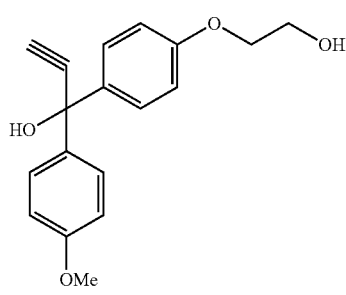 [SMILES: C#CC(O)(c1ccc(OC)cc1)c1ccc(OCCO)cc1] |

TABLE 12
| Example | Naphthol compound | Propargyl alcohol compound |
| --- | --- | --- |
| 33 | 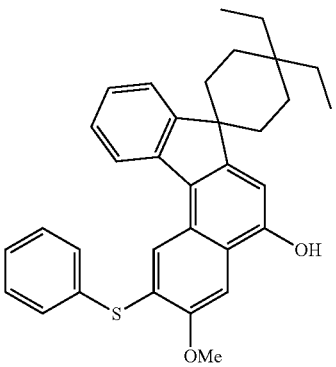 [SMILES: CCC1(CC)CCC2(CC1)c1ccccc1-c1c2cc(O)c2cc(OC)c(Sc3ccccc3)cc12] | 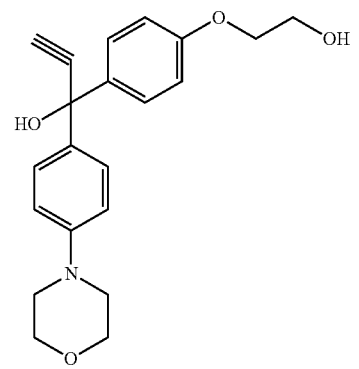 [SMILES: C#CC(O)(c1ccc(OCCO)cc1)c1ccc(N2CCOCC2)cc1] |
| 34 | 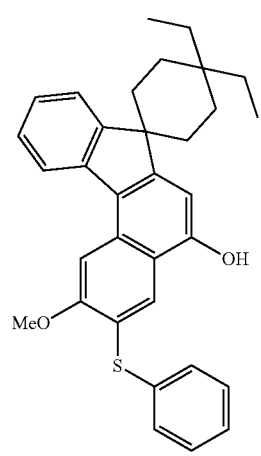 [SMILES: CCC1(CC)CCC2(CC1)c1ccccc1-c1c2cc(O)c2cc(Sc3ccccc3)c(OC)cc12] | 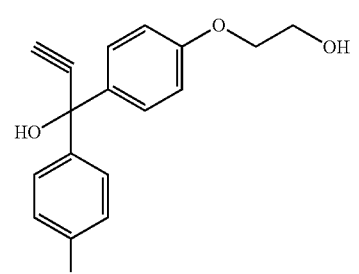 |
| 35 | 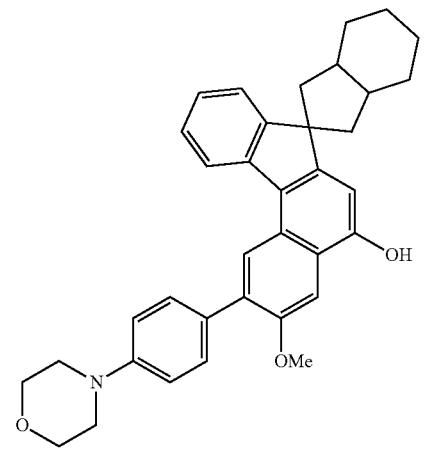 [SMILES: COc1cc2c(O)cc3c(c2cc1-c1ccc(N2CCOCC2)cc1)-c1ccccc1C31CC2CCCCC2C1] | 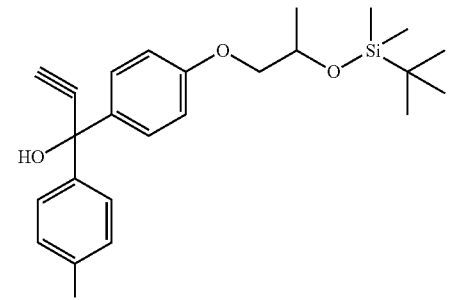 |

TABLE 12-continued

| Example | Naphthol compound | Propargyl alcohol compound |
| --- | --- | --- |
| 36 | | |
| 37 | | |

TABLE 13

| Example | Precursor | Product |
| --- | --- | --- |
| 28 | | |

TABLE 13-continued
| Example | Precursor | Product |
|---|---|---|
| 29 | 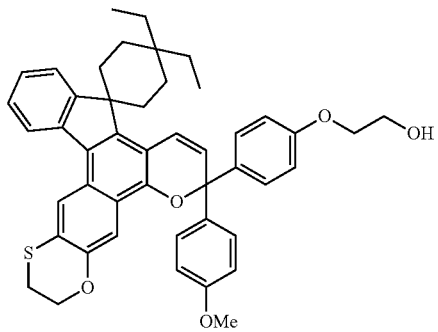 [SMILES: CCC1(CC)CCC2(CC1)c1ccccc1-c1c2c2c(c3cc4c(cc13)SCCO4)OC(c1ccc(OC)cc1)(c1ccc(OCCO)cc1)C=C2] | 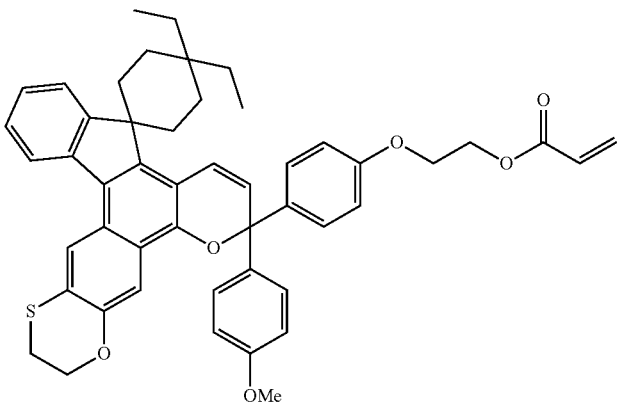 [SMILES: C=CC(=O)OCCOc1ccc(C2(c3ccc(OC)cc3)C=Cc3c4c(c5cc6c(cc5c3O2)OCCS6)-c2ccccc2C42CCC(CC)(CC)CC2)cc1] |
| 30 | 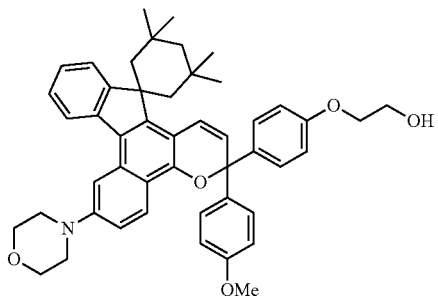 [SMILES: COc1ccc(C2(c3ccc(OCCO)cc3)C=Cc3c4c(c5cc(N6CCOCC6)ccc5c3O2)-c2ccccc2C42CC(C)(C)CC(C)(C)C2)cc1] | 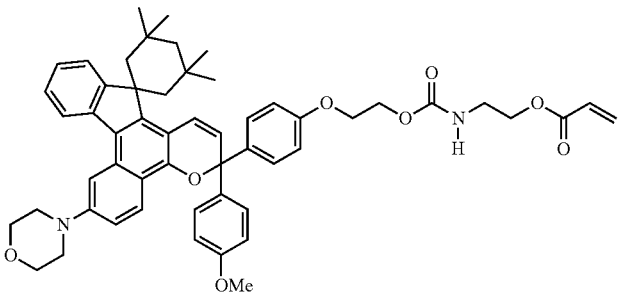 [SMILES: C=CC(=O)OCCNC(=O)OCCOc1ccc(C2(c3ccc(OC)cc3)C=Cc3c4c(c5cc(N6CCOCC6)ccc5c3O2)-c2ccccc2C42CC(C)(C)CC(C)(C)C2)cc1] |
| 31 | 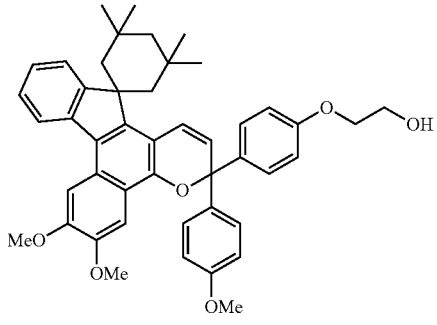 [SMILES: COc1ccc(C2(c3ccc(OCCO)cc3)C=Cc3c4c(c5cc(OC)c(OC)cc5c3O2)-c2ccccc2C42CC(C)(C)CC(C)(C)C2)cc1] | 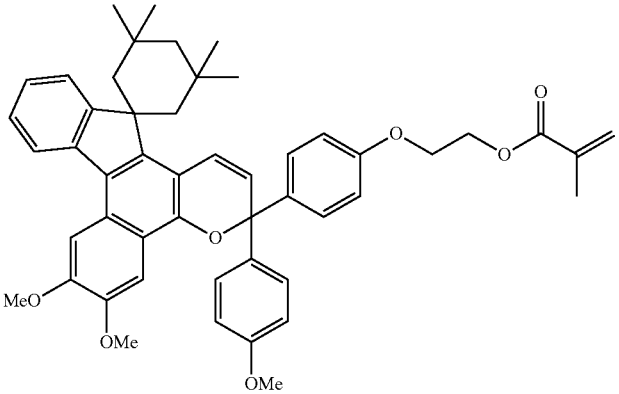 [SMILES: C=C(C)C(=O)OCCOc1ccc(C2(c3ccc(OC)cc3)C=Cc3c4c(c5cc(OC)c(OC)cc5c3O2)-c2ccccc2C42CC(C)(C)CC(C)(C)C2)cc1] |
| 32 | 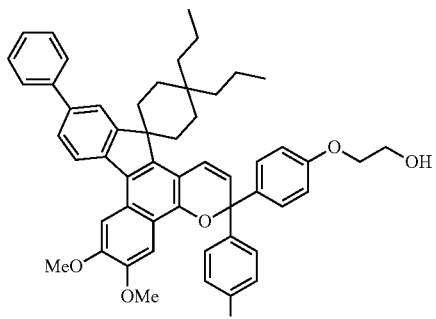 | 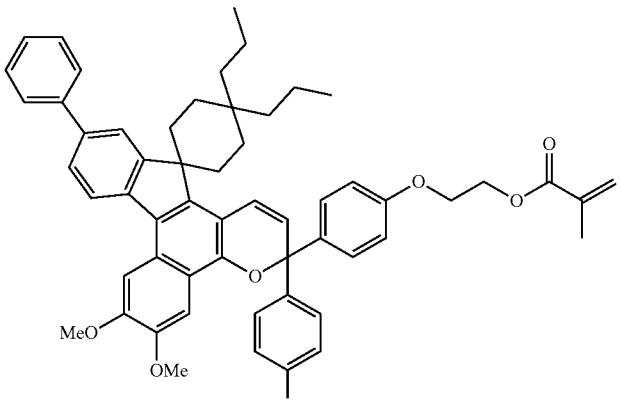 |

TABLE 14

| Example | Precursor | Product |
|---|---|---|
| 33 | | |
| 34 | | |

TABLE 14-continued
| Example | Precursor | Product |
|---|---|---|
| 35 | 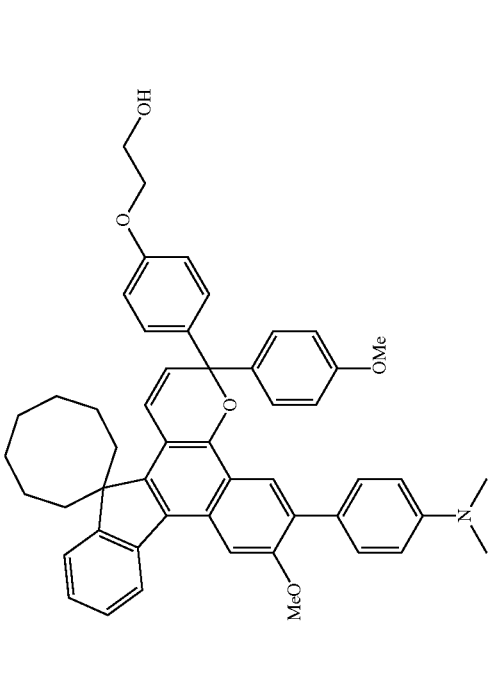 | 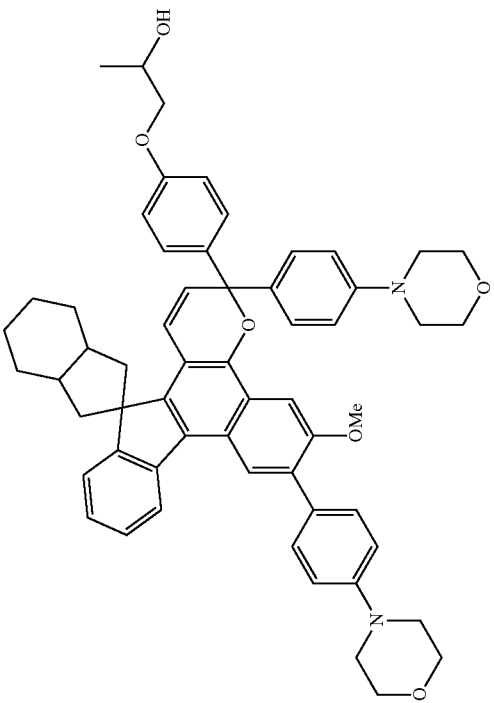 |
| 36 | 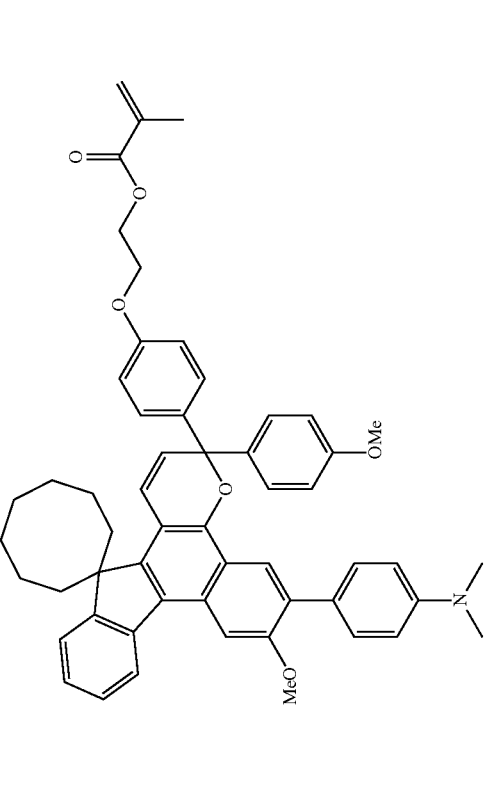 | 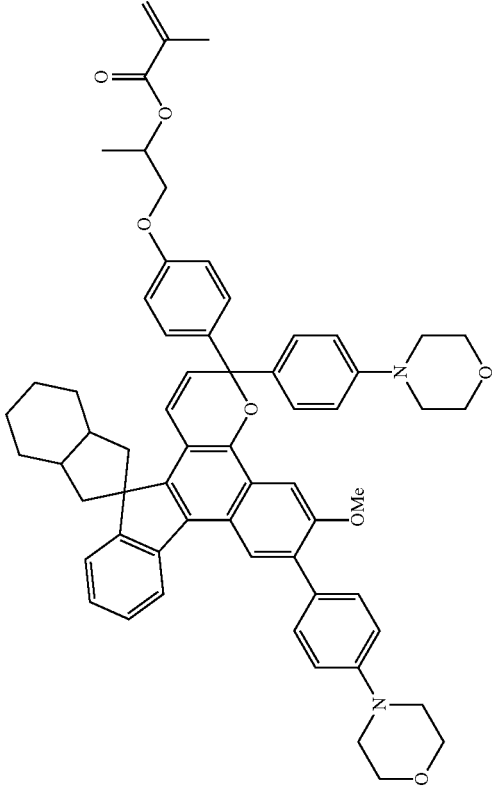 |

TABLE 14-continued

| Example | Precursor | Product |
|---|---|---|
| 37 | (structure with OH terminus) | (structure with methacrylate terminus) |

TABLE 15

| Example | Compound No. | Calculated value | | | | Measured value | | | | 1H-NMR |
|---|---|---|---|---|---|---|---|---|---|---|
| | | C | H | N | S | C | H | N | S | |
| 28 | 28 | 75.06 | 6.51 | 1.48 | — | 75.15 | 6.61 | 1.45 | — | δ0-5.0 ppm 39 H |
| | | | | | | | | | | δ5.0-9.0 ppm 22 H |
| 29 | 29 | 76.94 | 6.32 | — | 4.19 | 76.89 | 6.38 | — | 4.21 | δ0-5.0 ppm 29 H |
| | | | | | | | | | | δ5.0-9.0 ppm 19 H |
| 30 | 30 | 75.15 | 6.77 | 3.25 | — | 75.17 | 6.82 | 3.21 | — | δ0-5.0 ppm 38 H |
| | | | | | | | | | | δ5.0-9.0 ppm 20 H |
| 31 | 31 | 78.51 | 6.85 | — | — | 78.47 | 6.88 | — | — | δ0-5.0 ppm 34 H |
| | | | | | | | | | | δ5.0-9.0 ppm 18 H |
| 32 | 32 | 80.16 | 6.96 | — | — | 80.09 | 6.99 | — | — | δ0-5.0 ppm 36 H |
| | | | | | | | | | | δ5.0-9.0 ppm 22 H |
| 33 | 33 | 77.43 | 6.50 | 1.58 | 3.63 | 77.36 | 6.57 | 1.56 | 3.61 | δ0-5.0 ppm 33 H |
| | | | | | | | | | | δ5.0-9.0 ppm 24 H |
| 34 | 34 | 78.36 | 6.46 | — | 3.80 | 78.37 | 6.41 | — | 3.81 | δ0-5.0 ppm 31 H |
| | | | | | | | | | | δ5.0-9.0 ppm 23 H |
| 35 | 35 | 78.46 | 6.80 | 2.95 | — | 78.41 | 6.82 | 2.96 | — | δ0-5.0 ppm 42 H |
| | | | | | | | | | | δ5.0-9.0 ppm 22 H |
| 36 | 36 | 79.97 | 6.71 | 1.70 | — | 79.93 | 6.68 | 1.72 | — | δ0-5.0 ppm 33 H |
| | | | | | | | | | | δ5.0-9.0 ppm 22 H |
| 37 | 37 | 84.03 | 7.19 | — | — | 84.09 | 7.18 | — | — | δ0-5.0 ppm 34 H |
| | | | | | | | | | | δ5.0-9.0 ppm 18 H |

Examples 38 to 50

Photochromic contact lenses were produced and evaluated in the same manner as in Example 11.

The results are shown in Table 16. As in Table 8, in Table 16, the numbers of the compounds and the numbers of Examples coincide with each other. For example, the compound No. 25 is the chromene compound synthesized in Example 25.

TABLE 16

| Example | Compound No | $\lambda_{max}$ (nm) | $A_{36}$ (—) | $\tau_{1/2}$ (sec) | $A_0/A_{50} \times 100$ (%) | Elution ratio (%) |
|---|---|---|---|---|---|---|
| 38 | 25 | 469 | 0.44 | 26 | 88 | 1.2 |
| | | 577 | 0.56 | 26 | 87 | |
| 39 | 26 | 448 | 0.40 | 34 | 86 | 1.0 |
| | | 560 | 0.27 | 34 | 86 | |
| 40 | 27 | 438 | 0.35 | 31 | 83 | 1.3 |
| | | 571 | 0.50 | 31 | 83 | |
| 41 | 28 | 450 | 0.61 | 19 | 86 | 1.1 |
| | | 560 | 0.50 | 19 | 86 | |
| 42 | 29 | 443 | 0.44 | 34 | 85 | 0.8 |
| | | 547 | 0.53 | 34 | 84 | |
| 43 | 30 | 484 | 0.94 | 25 | 82 | 1.1 |
| | | 538 | 0.85 | 25 | 83 | |
| 44 | 31 | 463 | 0.50 | 15 | 81 | 1.3 |
| | | 560 | 0.43 | 15 | 82 | |
| 45 | 32 | 462 | 0.44 | 10 | 80 | 1.5 |
| | | 565 | 0.32 | 10 | 80 | |
| 46 | 33 | 476 | 0.29 | 14 | 83 | 0.9 |
| | | 581 | 0.35 | 14 | 84 | |
| 47 | 34 | 449 | 0.52 | 30 | 80 | 1.2 |
| | | 560 | 0.42 | 29 | 81 | |
| 48 | 35 | 486 | 0.64 | 20 | 83 | 1.4 |
| | | 583 | 0.61 | 20 | 84 | |
| 49 | 36 | 451 | 0.61 | 56 | 81 | 1.1 |
| | | 559 | 0.45 | 55 | 81 | |
| 50 | 37 | 444 | 0.44 | 52 | 80 | 1.3 |
| | | 550 | 0.87 | 53 | 81 | |

As can be seen from Table 16, the chromene compound of the present invention is excellent in durability, and is reduced in elution amount.

Examples 51 and 52, and Comparative Examples 4 and 5

Evaluation of Hydrolysis Resistance

4 Milliliters of 2-propanol was added to 10 mg of the radical-polymerizable chromene compound (Example 27 (the compound No. 27) or Example 34 (the compound No. 34)), and the mixture was stirred. After that, 0.5 mL of a 10 mass % aqueous solution of sodium hydroxide was added to the mixture, and the whole was stirred at room temperature for 1.5 hours.

After the stirring at room temperature, the hydrolysis conversion ratio of the chromene compound was calculated by analyzing the resultant through use of high performance liquid chromatography (HPLC).

Hydrolysis conversion ratio: (precursor chromene compound)/(precursor chromene compound+ radical-polymerizable chromene compound)× 100

A lower value of the hydrolysis conversion ratio means that the chromene compound is more excellent in hydrolysis resistance.

The term "precursor chromene compound" refers to a compound before the introduction of a polymerizable group, the compound having a hydroxy group at a terminal thereof. The precursor chromene compound is a compound produced by hydrolyzing a group having the polymerizable group in the polymerizable chromene compound.

For comparison, the compound represented by the formula (A) and a compound represented by the following formula (D) were used, and were each similarly evaluated for its hydrolysis resistance.

Those results are summarized in Table 17.

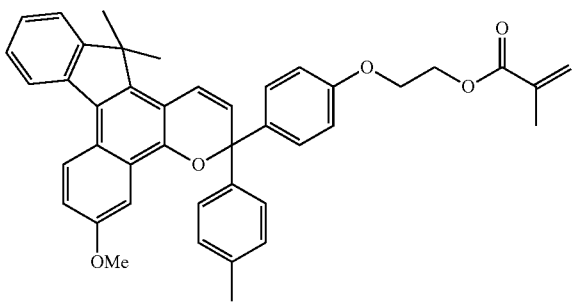

(D)

TABLE 17

| | Compound No | Hydrolysis conversion ratio (%) |
|---|---|---|
| Example 51 | 27 | 25 |
| Example 52 | 34 | 17 |
| Comparative Example 4 | A | 100 |
| Comparative Example 5 | D | 92 |

As is apparent from Table 17, the chromene compound of the present invention is excellent in hydrolysis resistance. In particular, the results of Examples and Comparative Example 5 showed that when the chromene compound of the present invention and the compound of Comparative Example had the same group as the group having the radical-polymerizable group, the chromene compound of the present invention was superior in hydrolysis resistance to the compound of Comparative Example. The foregoing means that when a spiro ring structure is arranged at the 13-position of the chromene compound, the steric crowding of the ester bond moiety thereof becomes larger to suppress the occurrence of the hydrolysis thereof.

The invention claimed is:

1. A chromene compound represented by the following formula (1):

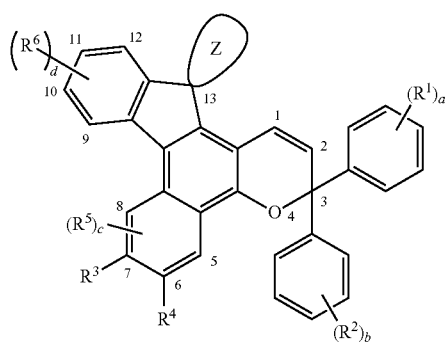

(1)

where $R^1$ and $R^2$ each independently represent a group having a radical-polymerizable group, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a hetero-cyclic group, a cyano group, a halogen atom, an alkylthio group having 1 to 6 carbon atoms, or an arylthio group having 6 to 10 carbon atoms that may have a substituent, "a" represents an integer of from 0 to 5, and "b" represents an integer of from 0 to 5, provided that a+b=1 to 10, at least one of $R^1$ or $R^2$ represents the group having the radical-polymerizable group, the group having the radical-polymerizable group consists of a group represented by the following formula (2):

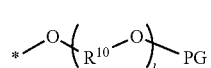

(2)

where $R^{10}$ represents a linear or branched alkylene group having 1 to 10 carbon atoms, "l" represents an integer of from 0 to 50, and when "l" represents 2 or more, unit groups in "l" pairs of parentheses may be groups identical to or different from each other,

* represents a direct bond to the phenyl ring, and

PG represents the radical-polymerizable group, wherein the radical-polymerizable group is selected from the group consisting of a vinyl group, a 1-chlorovinyl group, an allyl group, a styryl group, a (meth) acrylic group, a 2-(methacryloxy) ethylcarbamyl group, a 2-(methacryloxy) ethoxycarbonyl group, and a crotyl group, a ring Z represented by the following formula (Z), the ring being spiro-bonded to a carbon atom at a 13-position of the formula (1):

(Z)

is an aliphatic cyclic group that may have a substituent, the group having 3 to 20 carbon atoms for forming the ring together with the carbon atom at the 13-position, a condensed polycyclic group obtained by condensing the aliphatic cyclic group with an aromatic ring or an aromatic heterocycle that may have a substituent, a heterocyclic group that may have a substituent, the group having 3 to 20 atoms for forming the ring together with the carbon atom at the 13-position, or a condensed polycyclic group obtained by condensing the heterocyclic group with an aromatic ring or an aromatic heterocycle that may have a substituent, $R^3$ represents a hydrogen atom, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, a cyano group, a halogen atom, an alkylthio group having 1 to 6 carbon atoms, an arylthio group having 6 to 10 carbon atoms that may have a substituent, a nitro group, a formyl group, a hydroxycarbonyl group, an alkylcarbonyl group having 2 to 7 carbon atoms, an alkoxycarbonyl group having 2 to 7 carbon atoms, an aralkyl group having 7 to 11 carbon atoms that may have a substituent, an aralkoxy group having 7 to 11 carbon atoms that may have a substituent, an aryloxy group having 6 to 12 carbon atoms that may have a substituent, an aryl group having 6 to 12 carbon atoms that may have a substituent, a heteroaryl group having 3 to 12 carbon atoms that may have a substituent, a thiol group, an alkoxyalkylthio group having 2 to 9 carbon atoms, a haloalkylthio group having 1 to 6 carbon atoms, or a cycloalkylthio group having 3 to 8 carbon atoms, $R^4$ represents a hydrogen atom, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a heterocyclic group, a cyano group, a halogen atom, an alkylthio group having 1 to 6 carbon atoms, an arylthio group having 6 to 10 carbon atoms that may have a substituent, a nitro group, a formyl group, a hydroxycarbonyl group, an alkylcarbonyl group having 2 to 7 carbon atoms, an alkoxycarbonyl group having 2 to 7 carbon atoms, an aralkyl group having 7 to 11 carbon atoms that may have a substituent, an aralkoxy group having 7 to 11 carbon atoms that may have a substituent, an aryloxy group having 6 to 12 carbon atoms that may have a substituent, an aryl group having 6 to 12 carbon atoms that may have a substituent, a heteroaryl group having 3 to 12 carbon atoms that may have a substituent, a thiol group, an alkoxyalkylthio group having 2 to 9 carbon atoms, a haloalkylthio group having 1 to 6 carbon atoms, or a cycloalkylthio group having 3 to 8 carbon atoms, and $R^3$ and $R^4$ may form a ring represented by the following formula (3) together:

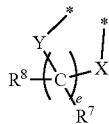

(3)

where * represents a carbon atom at a 6-position or a 7-position thereof, one, or each of both, of X and Y represents a sulfur atom, a methylene group, an oxygen atom, or a group represented by the following formula:

where $R^9$ represents a hydrogen atom, a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an aryl group having 6 to 12 carbon atoms that may have a substituent, or a heteroaryl group having 3 to 12 carbon atoms that may have a substituent, $R^7$ and $R^8$ each independently represent a hydroxy group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group, a cyano group, a nitro group, a formyl group, a hydroxycarbonyl group, an alkylcarbonyl group having 2 to 7 carbon atoms, an alkoxycarbonyl group having 2 to 7 carbon atoms, a halogen atom, an aralkyl group having 7 to 11 carbon atoms that may have a substituent, an aralkoxy group having 7 to 11 carbon atoms that may have a substituent, an aryl group having 6 to 12 carbon atoms that may have a substituent, a thiol group, an alkylthio group having 1 to 6 carbon atoms, an alkoxyalkylthio group having 2 to 9 carbon atoms, a haloalkylthio group having 1 to 6 carbon atoms, a cycloalkylthio group having 3 to 8 carbon atoms, or an arylthio group having 6 to 10 carbon atoms that may have a substituent, and $R^7$ and $R^8$ may form an aliphatic ring together with a carbon atom to which $R^7$ and $R^8$ are bonded, and "e" represents an integer of from 1 to 3, $R^5$ represents a hydroxy group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group, a cyano group, a nitro group, a formyl group, a hydroxycarbonyl group, an alkylcarbonyl group having 2 to 7 carbon atoms, an alkoxycarbonyl group having 2 to 7 carbon atoms, a halogen atom, an aralkyl group having 7 to 11 carbon atoms that may have a substituent, an aralkoxy group having 7 to 11 carbon atoms that may have a substituent, an aryl group having 6 to 12 carbon atoms that may have a substituent, a thiol group, an alkylthio group having 1 to 6 carbon atoms, an alkoxyalkylthio group having 2 to 9 carbon atoms, a haloalkylthio group having 1 to 6 carbon atoms, a cycloalkylthio group having 3 to 8 carbon atoms, or an arylthio group having 6 to 10 carbon atoms that may have a substituent, "c" represents an integer of from 0 to 2, and when "c" represents 2, $R^5$s may represent groups identical to or different from each other, $R^6$ represents a hydroxy group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group, a halogen atom, an aralkyl group having 7 to 11 carbon atoms that may have a substituent, an aralkoxy group having 7 to 11 carbon atoms that may have a substituent, a thiol group, an alkylthio group having 1 to 6 carbon atoms, an alkoxyalkylthio group having 2 to 9 carbon atoms, a haloalkylthio group having 1 to 6 carbon atoms, a cycloalkylthio group having 3 to 8 carbon atoms, or an arylthio group having 6 to 10 carbon atoms that may have a substituent, and "d" represents an integer of from 0 to 4, and when "d" represents 2 or more, $R^6$s may represent groups identical to or different from each other.

2. The chromene compound according to claim 1, wherein the ring Z represented by the formula (Z) has 6 to 12 carbon atoms for forming the ring together with the carbon atom at the 13-position.

3. The chromene compound according to claim 1, wherein the ring Z represented by the formula (Z) is a cyclic group selected from the following formulae:

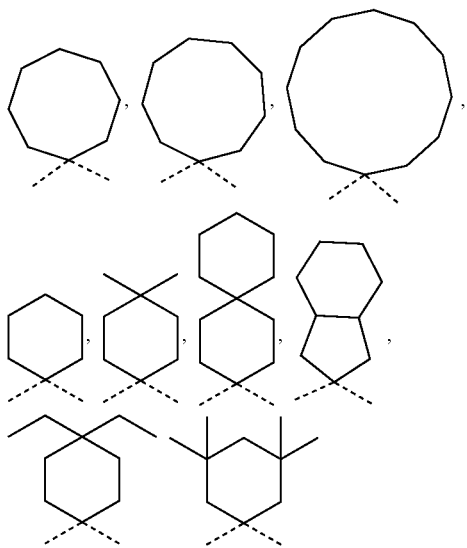

where a carbon atom having bonding hands represented by dotted lines is the carbon atom at the 13-position.

4. The chromene compound according to claim 1, wherein the number of the radical-polymerizable groups is 1.

5. A photochromic curable composition, comprising:
the chromene compound of claim 1; and
a polymerizable monomer except the chromene compound.

6. A photochromic optical article, comprising a polymer of the photochromic curable composition of claim 5.

7. A photochromic optical article, comprising, as at least part of constituent members, a polymer molded body obtained by polymerizing the photochromic curable composition of claim 5.

8. A photochromic optical article, comprising:
an optical substrate; and
a polymer film obtained by polymerizing the photochromic curable composition of claim 5, the polymer film serving as a coating layer configured to coat at least part of the optical substrate.

9. A photochromic optical article, comprising a polymer of the chromene compound of claim 1.

* * * * *